United States Patent
Henry et al.

(10) Patent No.: US 9,295,988 B2
(45) Date of Patent: Mar. 29, 2016

(54) MICROFLUIDIC CYTOCHEMICAL STAINING SYSTEM

(75) Inventors: Charles Henry, Fort Collins, CO (US);
Matthew Feirer, Fort Collins, CO (US);
Meghan Mensack, Thornton, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 322 days.

(21) Appl. No.: 13/415,341

(22) Filed: Mar. 8, 2012

(65) Prior Publication Data
US 2012/0230886 A1    Sep. 13, 2012

Related U.S. Application Data

(60) Provisional application No. 61/450,416, filed on Mar. 8, 2011.

(51) Int. Cl.
*B01L 99/00* (2010.01)
*B01L 3/00* (2006.01)
*G01N 1/31* (2006.01)

(52) U.S. Cl.
CPC .............. *B01L 3/5027* (2013.01); *G01N 1/312* (2013.01); *B01L 3/502715* (2013.01); *B01L 2300/0816* (2013.01); *B01L 2300/0822* (2013.01); *B01L 2300/0864* (2013.01)

(58) Field of Classification Search
CPC ....................... B01L 2300/0816; B01L 3/5027
USPC .................................................. 422/502, 503
See application file for complete search history.

(56) References Cited

U.S. PATENT DOCUMENTS

| 5,922,604 | A  | * | 7/1999  | Stapleton et al. ............... 436/46 |
| 6,225,109 | B1 | * | 5/2001  | Juncosa et al. ............. 435/288.5 |
| 6,915,679 | B2 | * | 7/2005  | Chien et al. .................. 73/54.01 |
| 2002/0187074 | A1 | * | 12/2002 | O'Connor et al. ......... 422/82.05 |
| 2004/0163958 | A1 | * | 8/2004  | Kao et al. ...................... 204/450 |

OTHER PUBLICATIONS

Cakal, C., et al., Development of a micro-total analysis system (μ-TAS) for the determination of catecholamines, Analytical and Bioanalytical Chemistry, 2010, 398, 1909-1917.
Scherer, J. R., et al., Design and operation of a portable scanner for high performance microchip capillary array electrophoresis, Review of Scientific Instruments, 2010, 81.
Ahn, C. H., et al., Disposable Smart Lab on a Chip for Point-of-Care Clinical Diagnostics, Proceedings of the Ieee, 2004, 92, 154-173.
Bhagat, A. A. S., et al., Microfluidics for cell separation, Medical &Biological Engineering & Computing, 2010, 48, 999-1014.

(Continued)

*Primary Examiner* — Paul Hyun
(74) *Attorney, Agent, or Firm* — Michael M. McGaw; Smith & Hopen, P.A.

(57) ABSTRACT

The present invention provides devices and associated methods to facilitate multiplexed staining on a slide. The use of multiplexed staining on a single slide allows for more accurate disease diagnosis while also conserving sample. A PDMS based cytology overlay was created that is capable of coupling on-chip morphological, cytochemical, and immunological staining. Morphological and cytochemical staining of blood smears, along with immunostaining of lymph node imprints, was carried out to demonstrate the application of this microfluidic cytology chip (μCC) device.

19 Claims, 21 Drawing Sheets

(56) References Cited

OTHER PUBLICATIONS

Liu, P. and R. A.Mathies, Integrated microfluidic systems for high-performance genetic analysis, Trends in Biotechnology, 2009, 27, 572-581.

Ohno, K., et al., Microfluidics: Applications for analytical purposes in chemistry and biochemistry, Electrophoresis, 2008, 29, 4443-4453.

Bhattacharyya, A. and C. M. Klapperich, Design and testing of a disposable microfluidic chemiluminescent immunoassay for disease biomarkers in human serum samples, Biomedical Microdevices, 2007, 9, 245-251.

Cheng, X. H., et al., A microfluidic device for practical label-free CD4+ T cell counting of HIVinfected subjects, Lab on a Chip, 2007, 7, 170-178.

James, T., et al., BioMEMS—Advancing the Frontiers of Medicine, Sensors, 2008, 8, 6077-6107.

McDonald, J. C., et al., Fabrication of microfluidic systems in poly(dimethylsiloxane), Electrophoresis, 2000, 21, 27-40.

J. C. McDonald and G. M. Whitesides, Poly(dimethylsiloxane) as a Material for Fabricating Microfluidic Devices, Acc Chem Res, 2002, 35, 491-499.

S. K. Sia and G. M. Whitesides, Microfluidic devices fabricated in poly(dimethylsiloxane) for biological studies, Electrophoresis, 2003, 24, 3563-3576.

Liu, Y., et al., Dynamic Coating Using Polyelectrolyte Multilayers for Chemical Control of Electroosmotic Flow in Capillary Electrophoresis Microchips, Anal Chem, 2000, 72, 5939-5944.

Liu, Y., et al., Simple and Sensitive Electrode Design for Microchip Electrophoresis/Electrochemistry, Anal Chem, 2004, 76, 1513-1517.

Banham, A. H., et al., Expression of the FOXP1 Transcription Factor is Strongly Associated with Inferior Survival in Patients with Diffuse Large B-Call Lymphoma, Clin Cancer Res, 2005, 11, 1065-1072.

Hoeller, S., et al., FOXP1 protein overexpression is associated with inferior outcome in nodal diffuse large B-cell lymphomas with non-germinal centre phenotype, independent of gains and structural aberrations at 3p14.1 Histopathology, 2010, 57, 73-80.

Valli, V., et al., Optimizing methods in immunocytochemistry: one laboratory's experience Vet Clin Pathol, 2009, 38, 261-269.

Ponce, F., et al., High-Grade Canine T-cell Lymphoma/Leukemia with Plasmacytoid Morphology: A Clinical Pathological Study of Nine Cases, J Vet Diagn Invest, 2003, 15, 330-337.

Gomori, G., Microtechnical Demostration of Iron: A Criticism of its Methods, Am J Pathol, 1936, 12, 655-664 651.

Kim, J., et al., Hydrophobic Recovery of Polydimethylsiloxane Elastomer Exposed to Partial Electrical Discharge, Journal of Colloid and Interface Science, 2000, 226, 231-236.

Kim, J., et al., The Mechanisms of Hydrophobic Recovery of Polydimethylsiloxane Elastomers Exposed to Partial Electrical Discharges, Journal of Colloid and Interface Science, 2001, 244, 200-207.

Vickers, J. A., et al., Generation of Hydrophilic Poly(dimethylsiloxane) for High-Performance Microchip Electrophoresis, Anal Chem, 2006, 78, 7446-7452.

R. Lovchik, et al., Micro-immunohistochemistry using a microfluidic probe, Lab Chip, 2012, 12, 1040-1043.

\* cited by examiner

MICROFLUIDIC CYTOCHEMICAL STAINING SYSTEM

CROSS REFERENCE TO RELATED APPLICATIONS

This application claims priority to U.S. Provisional Patent Application 61/450,416, entitled, "Microfluidic Cytochemical Staining System", filed Mar. 8, 2011, the contents of which are herein incorporated by reference.

FIELD OF INVENTION

This invention relates to microscopic tissue analysis. More specifically, this invention relates to devices for multiplexed staining on a slide or other planar surface.

BACKGROUND OF THE INVENTION

Microscopic tissue analysis plays an extremely important role in the diagnosis of many diseases. With most incisional and excisional biopsy samples, tissues are fixed and embedded in paraffin blocks, allowing for the re-cutting of as many slides as necessary to ensure an accurate diagnosis. In contrast, the number of submitted slides for commonly obtained cytology samples, such as fine needle aspirates, tissue imprints, and fluid preparations are often limited, restricting the number of stains that can be used in diagnosis. If an additional cytochemical or immunocytological staining is deemed necessary, re-sampling is often required, resulting in increased costs, time to diagnosis, and additionally, increased patient stress. The present invention provides a novel approach to microscopic tissue analysis over-coming these limitations, and others, characterizing the prior art by allowing a single slide to be used for multiple assays, thereby stretching the use of a given sample while reducing the use of reagents and processing time, as will become apparent in the following disclosure.

SUMMARY OF INVENTION

The present invention provides devices and associated methods to facilitate multiplexed staining of a biological sample on a slide or other planar surface. The use of multiplexed staining on a single slide allows for more accurate disease diagnosis while also conserving sample. A PDMS based cytology overlay was created that is capable of coupling on-chip morphological, cytochemical, and immunological staining. Morphological and cytochemical staining of blood smears, along with immunostaining of lymph node imprints, was carried out to demonstrate the application of this microfluidic cytology chip (μCC) device. One important advantage of the μCC device is that the architecture creates an environment "continuous flow" of reagent. Recent efforts towards enhanced efficacy in macro-fluidic systems attempt to blow or vibrate puddles of reagent around on the surface of a slide. As an alternative, it is proposed to create a flow of reagent over the surface. This flow provides an inherent advantage in that the μCC device provides an environment where reagent is continuously moved over the sample. In essence, the system is able to put bio-targets into contact with a continuous flow of the markers that are seeking to find them on a microscopic level. In the hands of the clinician the technology should allow for a more comprehensive diagnosis, leading to a better life science outcome.

In a first aspect the present invention provides a microfluidic cytology chip (μCC) overlay device. The device has a substantially planar surface with dimensions analogous to those of a microscopic slide. The substantially planar surface allows the device to interface with the surface of a microscopic slide, or other planar surface, having a fixed sample on its surface. The substantially planar surface of the μCC overlay device has a first end with a plurality of holes and a second end with one or more holes. It also has a plurality of channels, equal in number to the plurality of holes at the first end, where each channel of the plurality of channels connects one of the plurality of holes at the first end to one of the one or more holes at the second end. When the μCC overlay device assembled to a slide or other complementary surface having a fixed sample, the plurality of holes at the first end forms a plurality of inlets and the one or more holes at the second end forms one or more outlets. Additionally, the plurality of channels forms a sealed conduit between the inlets and the outlets when the μCC overlay device is coupled to a microscopic slide or the like.

In an advantageous embodiment the μCC overlay device according to the first aspect is composed of a material such as polydimethylsiloxane (PDMS) or extracted PDMS.

In further advantageous embodiments the μCC overlay device according to the first aspect can include a coupling device to affix the μCC overlay device to a microscopic slide. The coupling device could be a clip, a sleeve, or a chamber. Additionally, the coupling device can include one or more integral inlet or outlet ports, and the inlet or outlet ports can be positioned on the coupling device to facilitate receipt within an inlet or outlet of the μCC overlay device. The coupling device could also be integral to the μCC overlay device.

The μCC overlay can be configured such that the device has a plurality of outlets, and each one of the plurality of channels can provide a fluid communication channel between a single inlet and a single outlet. Thus, each channel would have a dedicated outlet, rather than sharing an outlet with other channels.

The μCC overlay device according to the first aspect can have a substantially rectangular shape, similar to the microscope slide to which it interfaces, and the inlet and outlet holes can be spaced at opposing ends of the rectangle towards the most distant ends. In a similar fashion, the substantially planar surface of the μCC overlay device can approximate at least a portion of the substantially planar surface of the microscope slide.

In a second aspect the present invention provides additional embodiments of a μCC overlay device. The device according to the second aspect has a substantially planar sheet with opposing ends and a plurality of holes at a first end, at least one hole at an opposing end and a plurality of channels singularly linking each of the plurality of holes at the first end with the at least one hole at the opposing end. The plurality of holes at the first end form inlets and the at least one hole at an opposing end forms an outlet when overlay device is coupled to a complementary planar surface containing a sample. The plurality of channels provide sealed fluidic communication between the inlets and the at least one outlet when the overlay device is coupled to a complementary planar surface containing a sample.

In an advantageous embodiment the μCC overlay device according to the second aspect is composed of a material such as polydimethylsiloxane (PDMS) or extracted PDMS.

In further advantageous embodiments the μCC overlay device according to the second aspect can include a coupling device to affix the μCC overlay device to a microscopic slide. The coupling device could be a clip, a sleeve, or a chamber. Additionally, the coupling device can include one or more integral inlet or outlet ports, and the inlet or outlet ports can be positioned on the coupling device to facilitate receipt within an inlet or outlet of the μCC overlay device. The coupling device could also be integral to the μCC overlay device.

The μCC overlay can be configured such that the device has a plurality of outlets, and each one of the plurality of channels can provide a fluid communication channel between a single inlet and a single outlet. Thus, each channel would have a dedicated outlet, rather than sharing an outlet with other channels.

The μCC overlay device according to the second aspect can have a substantially rectangular shape, similar to the microscope slide to which it interfaces, and the inlet and outlet holes can be spaced at opposing ends of the rectangle towards the most distant ends. In a similar fashion, the substantially planar surface of the μCC overlay device can approximate at least a portion of the substantially planar surface of the microscope slide.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Multiplexed strategies for diagnostic and prognostic assessment are inherently more accurate. Unfortunately, current sample requirements for each cytological or immunological test limit the total number of assays that can be performed. One solution to this problem is to improve staining efficiency through miniaturization. Smaller, faster analysis systems have become increasingly employed since microscale total analysis systems (μTAS) devices first appeared in the late 1990s. [Cakal, C., et al., *Analytical and Bioanalytical Chemistry*, 2010, 398, 1909-1917; Scherer, J. R., et al., *Review of Scientific Instruments*, 2010, 81; Ahn, C. H., et al., *Proceedings of the Ieee*, 2004, 92, 154-173]μTAS technology is already widely incorporated in the field of cell biology. [Bhagat, A. A. S., et al., *Medical & Biological Engineering & Computing*, 2010, 48, 999-1014; Liu, P. and R. A. Mathies, *Trends in Biotechnology*, 2009, 27, 572-581; Ohno, K., et al., *Electrophoresis*, 2008, 29, 4443-4453] Incorporation of these technologies into common clinical practice, however, is still in the early stages. [Rosen, Y. and P. Gurman, *Current Pharmaceutical Biotechnology*, 2010, 11, 366-375; Dobson, M. G., et al., *Expert Review of Molecular Diagnostics*, 2007, 7, 359-370]μTAS devices have found application in the realm of clinical diagnosis, [Ahn, C. H., et al., *Proceedings of the Ieee*, 2004, 92, 154-173; Bhattacharyya, A. and C. M. Klapperich, *Biomedical Microdevices*, 2007, 9, 245-251; Cheng, X. H., et al., *Lab on a Chip*, 2007, 7, 170-178; James, T., et al., *Sensors*, 2008, 8, 6077-6107] and provide an added benefit, beyond merely scale, of reduced sample and reagent consumption (nL versus mL) and reduced analysis time (often minutes instead of hours). Furthermore, the use of miniaturized systems drastically reduces equipment cost since large, costly analyzers are no longer required.

These limitations of traditional whole slide staining make the development of a multi-channel, microfluidic staining system for clinical cytology slides all the more important. The development of a faster, more efficient system for the analysis of cell morphology, composition, and phenotyping will enable the diagnostician to make a faster, more accurate diagnosis; directly resulting in improved patient care and reduced healthcare costs. With this need delineated, a novel system was developed enabling the simultaneous performance and detection of multiple cytochemical and immunological-based stains on routinely prepared cytology samples. This microfluidic cytology chip (μCC) allows for faster and more accurate disease diagnosis, while requiring fewer overall samples and reduced reagent consumption. The development of this μCC, along with results of early morphological, cytochemical, and immunological staining is presented in the disclosure below.

Figure 1:
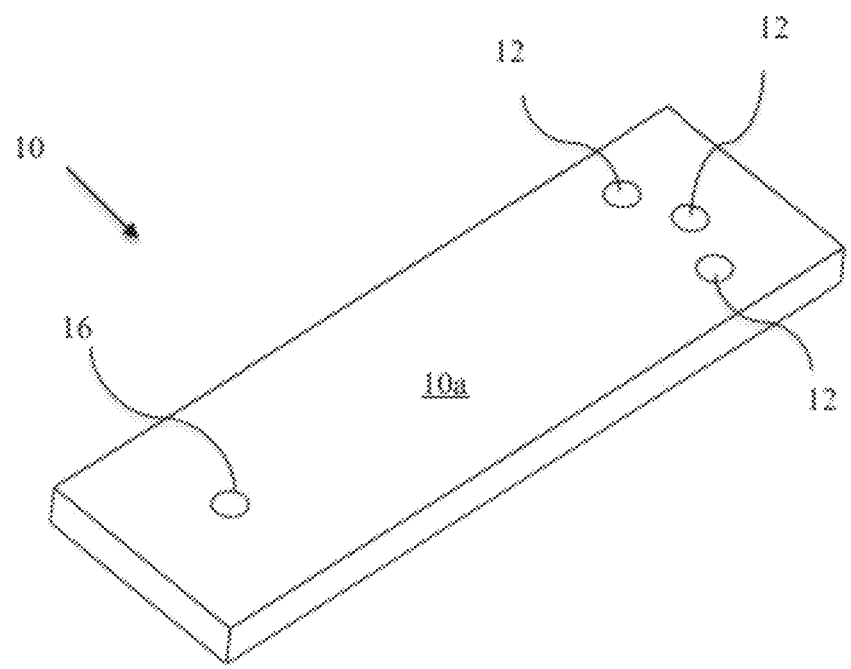
FIG. 1 is a perspective view of the top of an exemplary microfluidic cytology chip (μCC) overlay device.

Turning to the figures, FIG. 1 is an illustration of a microfluidic cytology chip (μCC) overlay device 10 according to aspects of the invention. A first side, or top side 10a, of μCC overlay device 10 is shown. At one end of the device there is shown three inlets 12, or holes, extending from the top side 10a of the μCC overlay device 10 through to the bottom side 10b of the μCC overlay device 10. At the opposite end of the device there is shown a single outlet 16, or hole, also extending from the top side 10a of the μCC overlay device 10 through to the bottom side 10b of the μCC overlay device 10.

Figure 2:
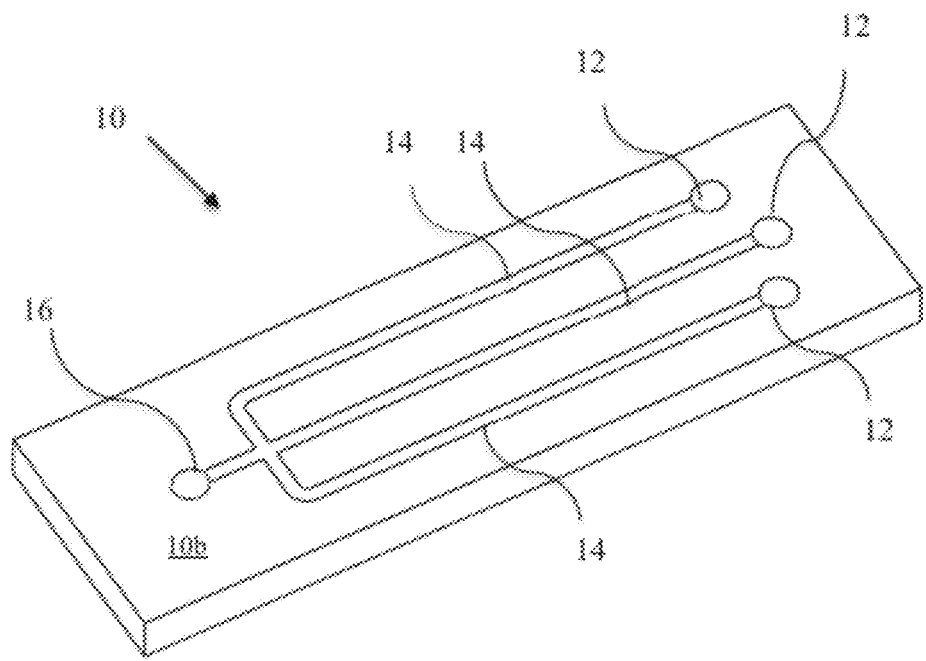
FIG. 2 is a perspective view of the bottom of the exemplary μCC overlay device shown in FIG. 1, illustrating three channels on the bottom of the slide, where each channel has its own inlet and shares an outlet with the other two channels.

FIG. 2 illustrates the bottom side 10b of the μCC overlay device 10 shown in FIG. 1. Following from FIG. 1, there are three inlets 12 at a first end of the μCC overlay device 10 and a single outlet at the opposite end of the device 10, all extending from the top side through to the bottom side. There are also three channels 14, each emanating from its own, dedicated inlet 12, while all of the channels terminate at the single outlet 16. The channels enable fluid communication as liquid reagents enter through one of the inlets 12, pass down the respective channel 14 and exit at the outlet 16.

Figure 3:
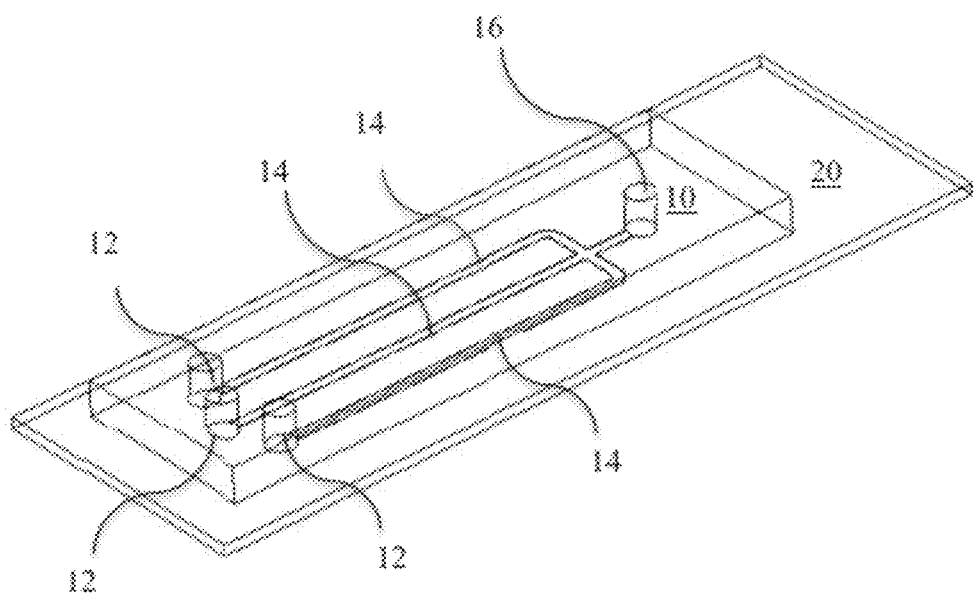
FIG. 3 is perspective view of a translucent μCC overlay device appended to a microscopic slide, illustrating the channels in proximity to the slide.
Figure 4:
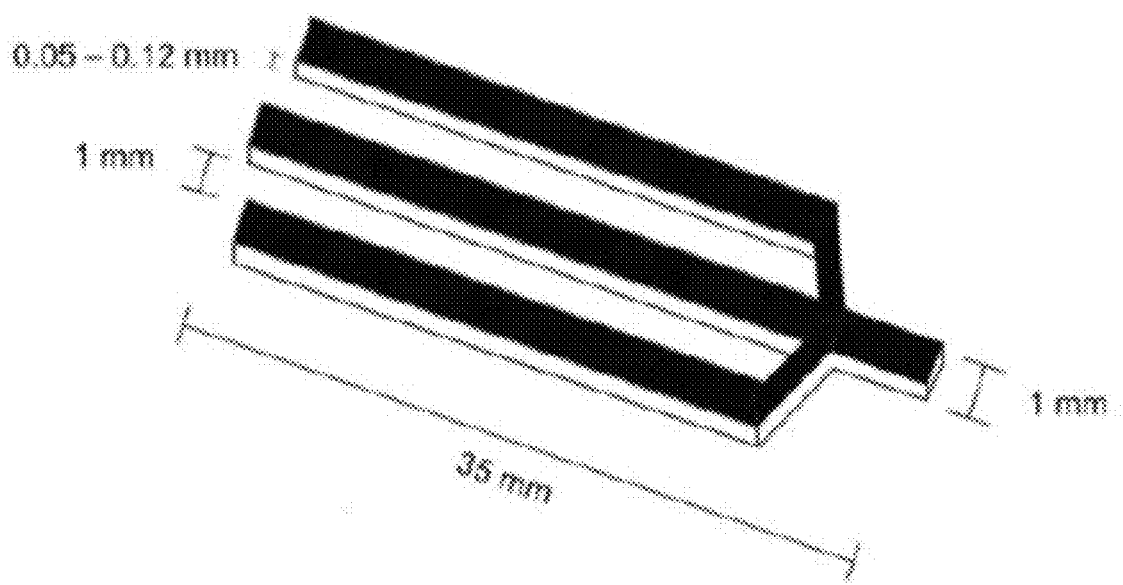
FIG. 4 is an illustration of the channel architecture of a μCC overlay device having three channels, with associated inlets, and a single outlet.
Figure 21:
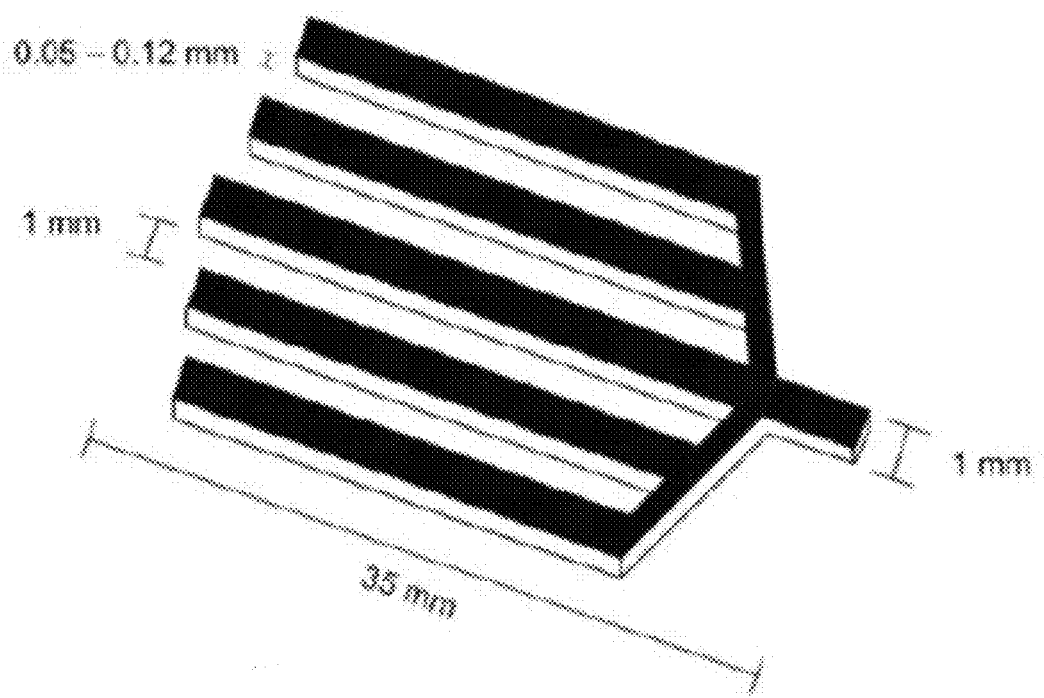
FIG. 21 is an illustration of the channel architecture of a microfluidic chip having five channels, with associated inlets, and a single outlet.

FIG. 3 shows a μCC overlay device 10 having the same "3 inlet-3 channel-1 outlet" architecture as the device illustrated in FIGS. 1 and 2. The device 10 is sitting on top of a microscopic slide 20. However, the μCC overlay device 10 of FIG. 3 is depicted as translucent, rather than opaque as in FIGS. 1 and 2, to show the arrangement of the channels 14 in relation to the slide 20. Accordingly, in FIG. 3 the top side 10a of the device 10 faces away from the slide, while the bottom side 10b of the device 10 is in contact with the slide 20. The contact between the bottom side 10b of the device 10 and the slide effectively seals the channels 14, with the exception on the openings at the inlet 12 and the outlet 16, thereby preventing leakage of reagents as the reagents pass down the channel 14 from the inlet 12 to the outlet 16. In the process of traversing the channel 14, the reagents are able to stain cells and other matter affixed to the slide 20. FIG. 4 shows exemplary channel dimensions of a "3 inlet-3 channel-1 outlet" μCC overlay device 10 as illustrated in FIGS. 1-3. The dimensions of a "5 inlet-5 channel-1 outlet" μCC overlay device is illustrated in FIG. 21.

Figure 5:
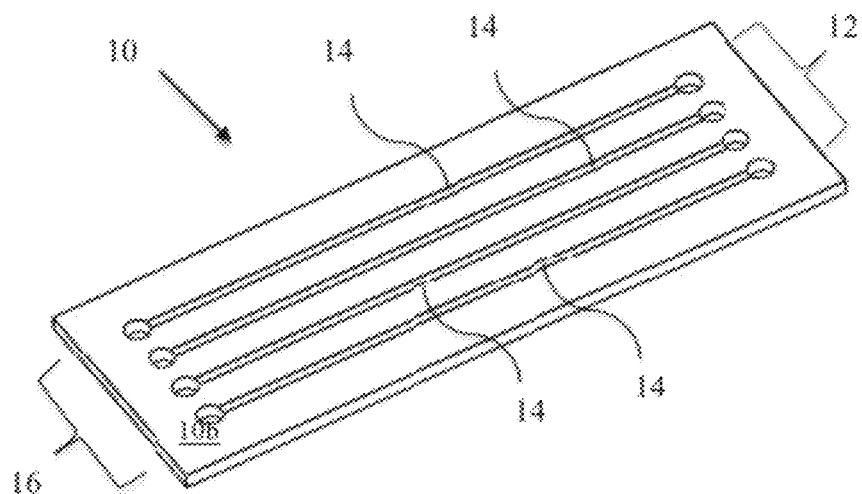
FIG. 5 is a perspective view of the bottom of an alternative embodiment of a μCC overlay device, illustrating four channels on the bottom of the slide, where each channel has its own inlet and outlet.

FIG. 5 is an illustration of an alternative embodiment of a microfluidic cytology chip (μCC) overlay device 10 according to further aspects of the invention. FIG. 5 provides an opaque illustration of the bottom side 10b of the μCC overlay device 10. At one end of the device there is shown four inlets 12, or holes, extending from the top side 10a (not shown for this configuration) of the μCC overlay device 10 through to the bottom side 10b of the μCC overlay device 10. At the opposite end of the device there is shown four outlets 16, or holes, also extending from the top side 10a (not shown) of the μCC overlay device 10 through to the bottom side 10b of the μCC overlay device 10. There are also four channels 14, each emanating from one of four inlets 12, and each terminating in one of four outlets 16. Thus, each channel 14 has its own dedicated inlet 12 and outlet 16. The channels enable fluid communication as liquid reagents enter through one of the inlets 12, pass down the respective channel 14 and exit at the associated outlet 16.

Figure 6:
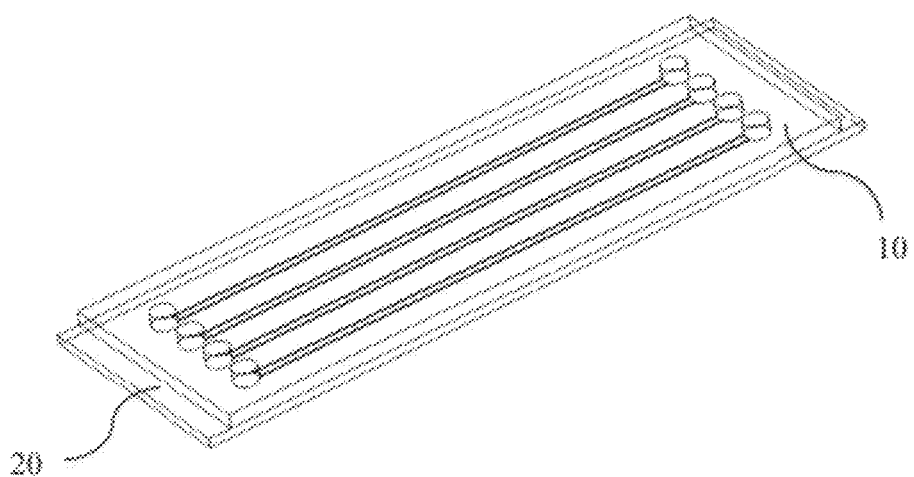
FIG. 6 is perspective view of a translucent μCC overlay device appended to a microscopic slide, illustrating a four-channel device having the channel architecture of the device illustrated in FIG. 5.

FIG. 6 shows a μCC overlay device 10 having the same "4 inlet-4 channel-4 outlet" architecture as the device illustrated in FIG. 5. The device 10 is sitting on top of a microscopic slide 20. However, the μCC overlay device 10 of FIG. 6 is depicted as translucent, rather than opaque as in FIG. 5, to show the arrangement of the channels 14 in relation to the slide 20. Accordingly, in FIG. 6 the top side 10a (not labeled) of the device 10 faces away from the slide, while the bottom side 10b (not labeled—see FIG. 5) of the device 10 is in contact with the slide 20. The contact between the bottom side 10b of the device 10 and the slide effectively seals the channels 14 (not labeled—see FIG. 5), with the exception on the openings at the inlet 12 (not labeled—see FIG. 5) and the outlet 16 (not labeled—see FIG. 5), thereby preventing leakage of reagents as the reagents pass down the channel 14 from the inlet 12 to the outlet 16. In the process of traversing the channel 14, the reagents are able to stain cells and other matter affixed to the slide 20.

Figure 20:
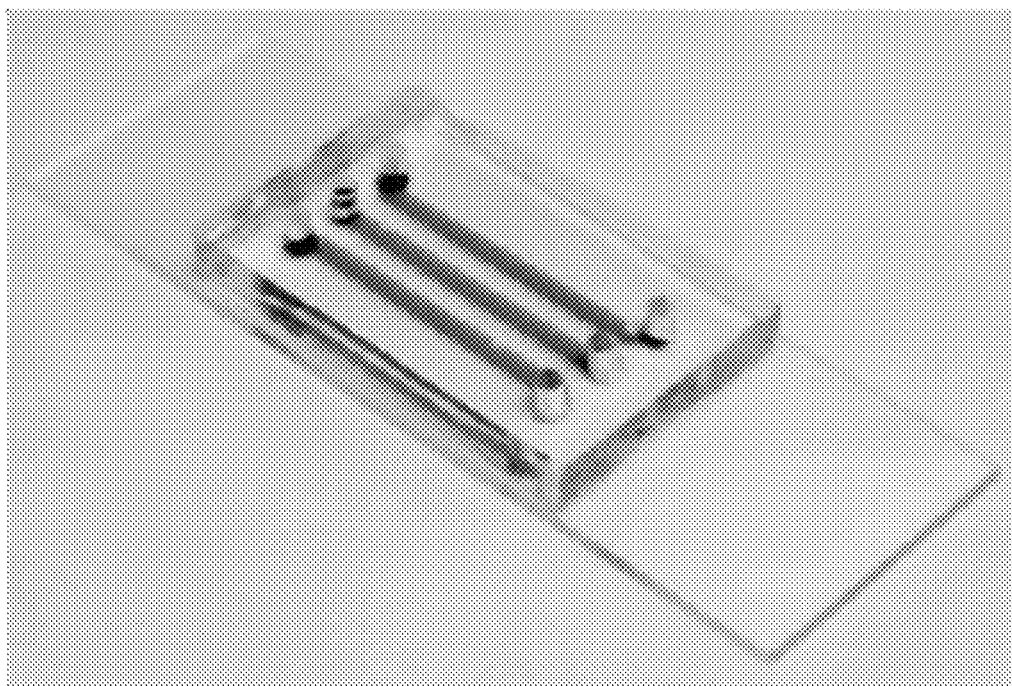
FIG. 20 is an image of a translucent microfluidic chip appended to a microscopic slide. The microfluidic chip has three channels, with associated inlets, and each channel has its own outlet. Dye is used to illustrate channel location and dimensions.
Figure 22:
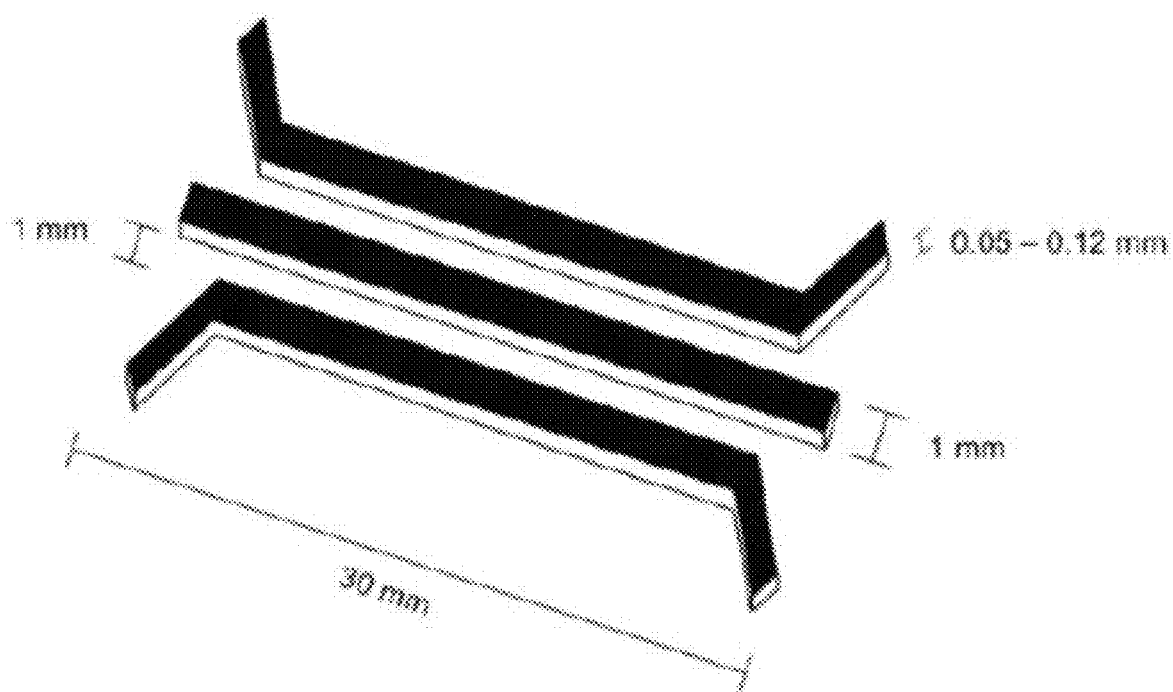
FIG. 22 is an illustration of the channel architecture of a microfluidic chip having three channels, with associated inlets, and each channel having its own outlet.

The dimensions of an exemplary "3 inlet-3 channel-3 outlet" μCC overlay device is illustrated in FIG. 22. FIG. 20 presents an image of such a "3 inlet-3 channel-3 outlet" μCC overlay device affixed to a microscopic slide. Stained reagent has been added to the channels of the device shown in FIG. 20 to facilitate the visualization of each of the three channels.

Figure 7:
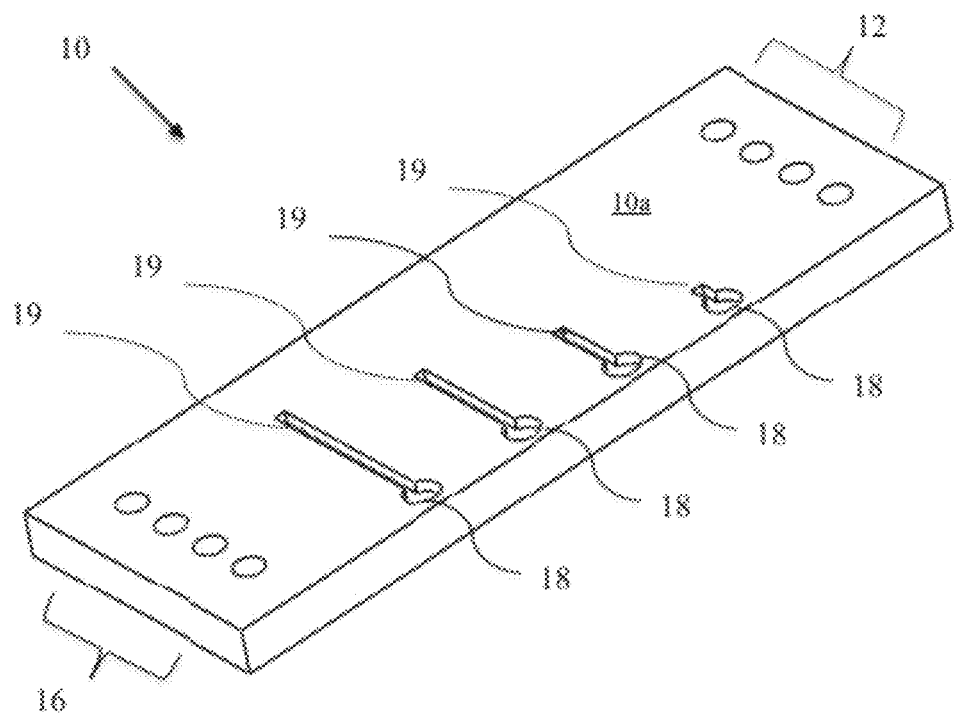
FIG. 7 is a perspective view of the top of an alternative embodiment of a μCC overlay device. The device has the same four-channel architecture as the device illustrated in FIG. 5, but adds four reagent reservoirs, and associated conduits, to the top of the device for the delivery of reagents to the channels below.

FIG. 7 is an illustration of a μCC overlay device 10 with reagent reservoirs 18 integral to the device. The illustration shows the top side 10a of the μCC overlay device 10. Reagent is loaded into the reagent reservoirs 18 where the reagent then traverses the μCC overlay device 10 via the conduit 19 on the top side 10a of the device 10 to a region directly above the respective channel 14 (not shown—see FIG. 8). Once above the channel, the conduit 19 perforates the μCC overlay device 10 allowing the reagent to pass through the device 10 to the channel 14 on the bottom side 10b of the μCC overlay device 10.

Figure 8:
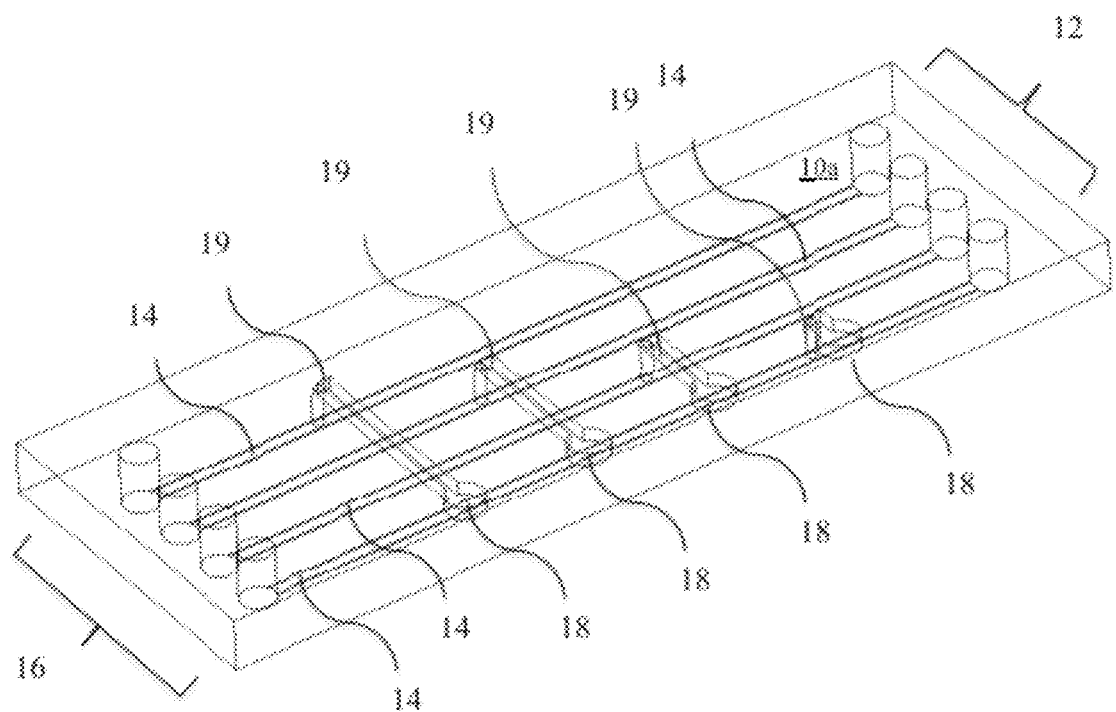
FIG. 8 is a perspective view of a translucent μCC overlay device as depicted in FIG. 7.

FIG. 8 provides a translucent illustration of the opaque device depicted in FIG. 7. The channels 14 on the bottom side 10b of the device are thereby evident, as are the perforations created by the conduit 19 passing from the top side 10a of the μCC overlay device 10 to the bottom side 10b of the device 10 where the conduit 19 delivers reagent to the channel 14.

Figure 9:
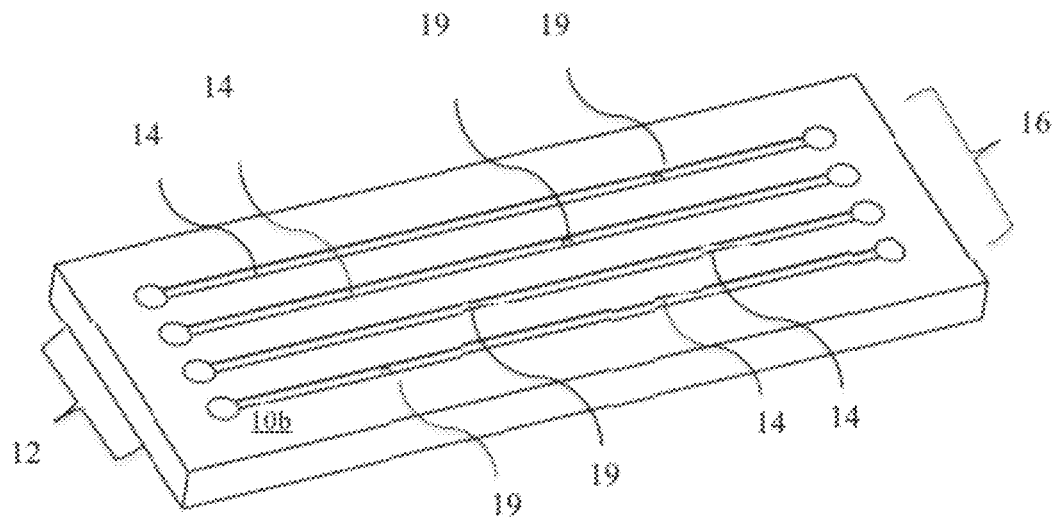
FIG. 9 is a perspective view of the bottom side of the μCC overlay device depicted in FIG. 7.
Figure 10:
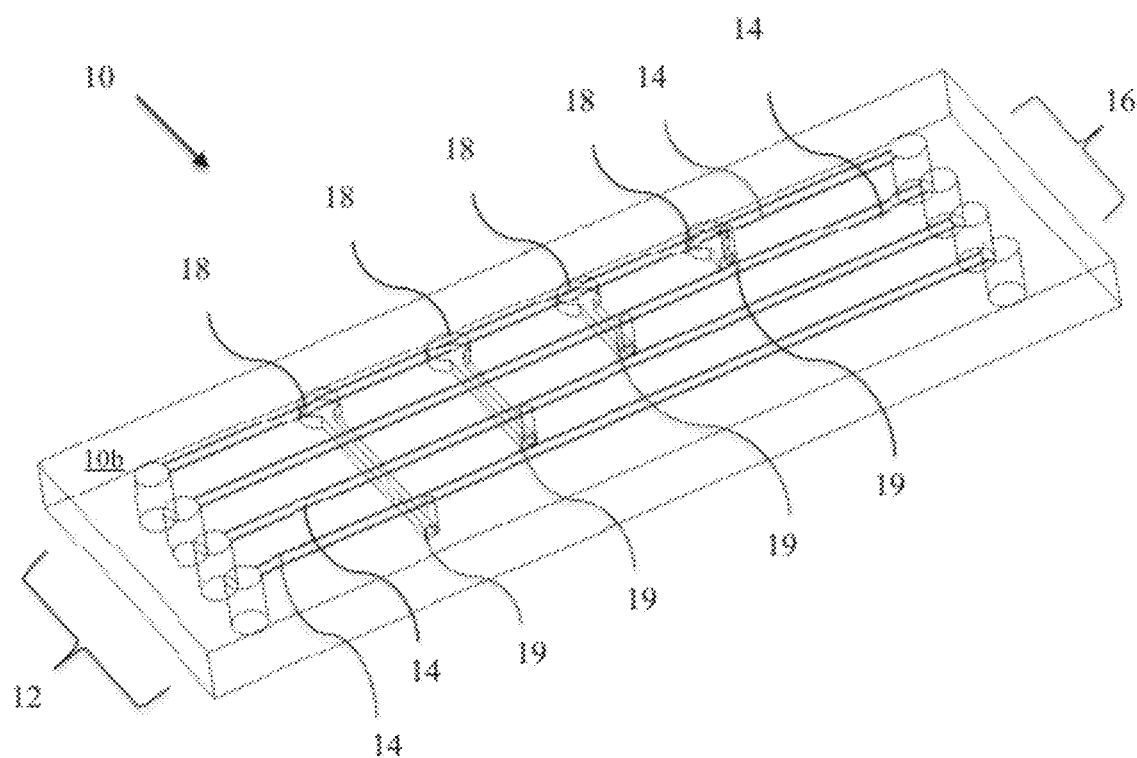
FIG. 10 is a perspective view of a translucent μCC overlay device as depicted in FIG. 9.

FIG. 9 is an illustration of the bottom side 10b of the μCC overlay device 10 depicted in FIG. 7. The conduits 19 are seen opening into the channels 14 on the bottom side 10b of the μCC overlay device 10. FIG. 10 provides a translucent illustration of the opaque device depicted in FIG. 9.

Figure 11:
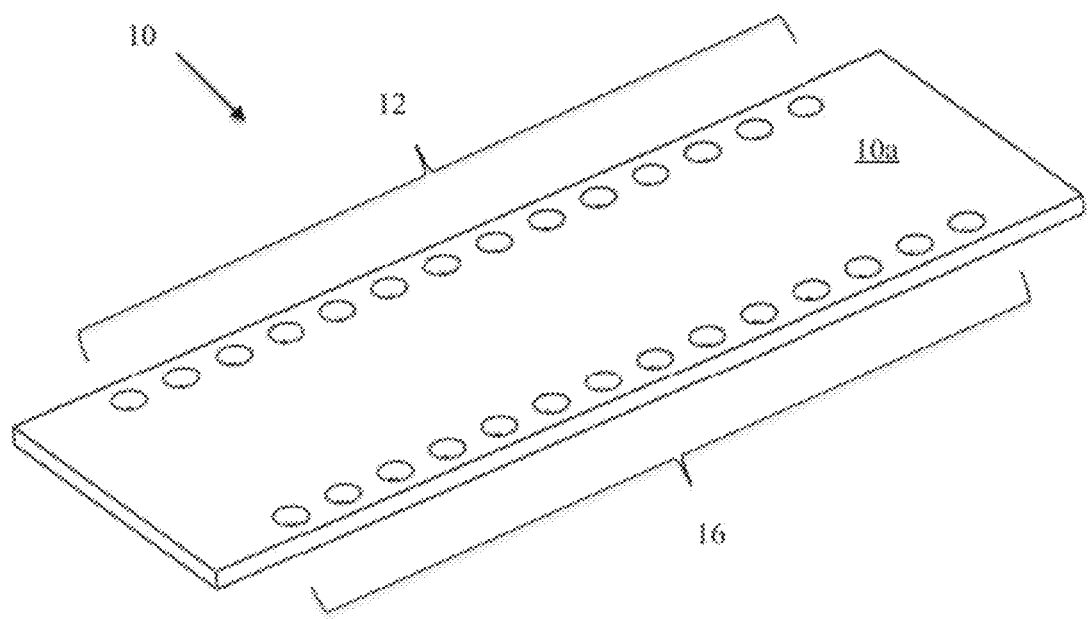
FIG. 11 is a perspective view of the top of an alternative embodiment of a μCC overlay device.

FIG. 11 is an illustration of top side 10a of a μCC overlay device 10 having a series of inlets 12 arranged across a long side of the device 10, with a series of outlets 16 arranged across an opposite side of the device 10. By arranging the inlet and the outlets in this manner the same slide can be used for more tests, but a smaller surface area of the sample is used for each given test.

Figure 12:
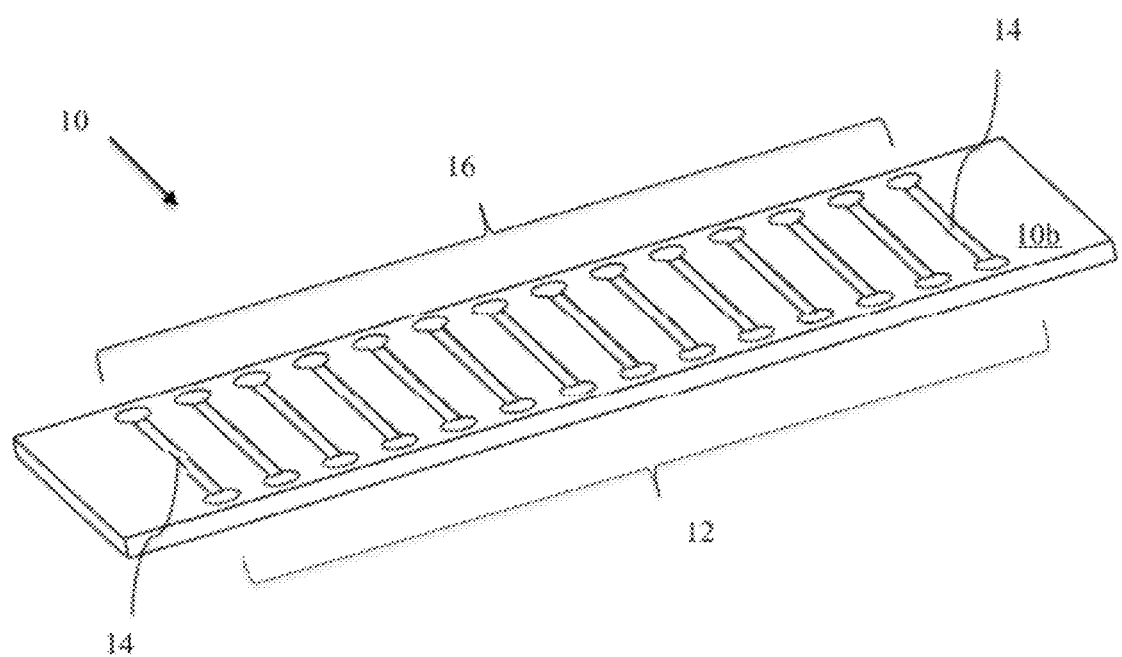
FIG. 12 is a perspective view of the bottom side of the μCC overlay device depicted in FIG. 11.

FIG. 12 is an illustration of bottom side 10b of a μCC overlay device 10 depicted in FIG. 11. The channels 14 along the bottom side 10b are evident traversing the width of the device 10 from the inlets 12 to the outlets 16.

Figure 13:
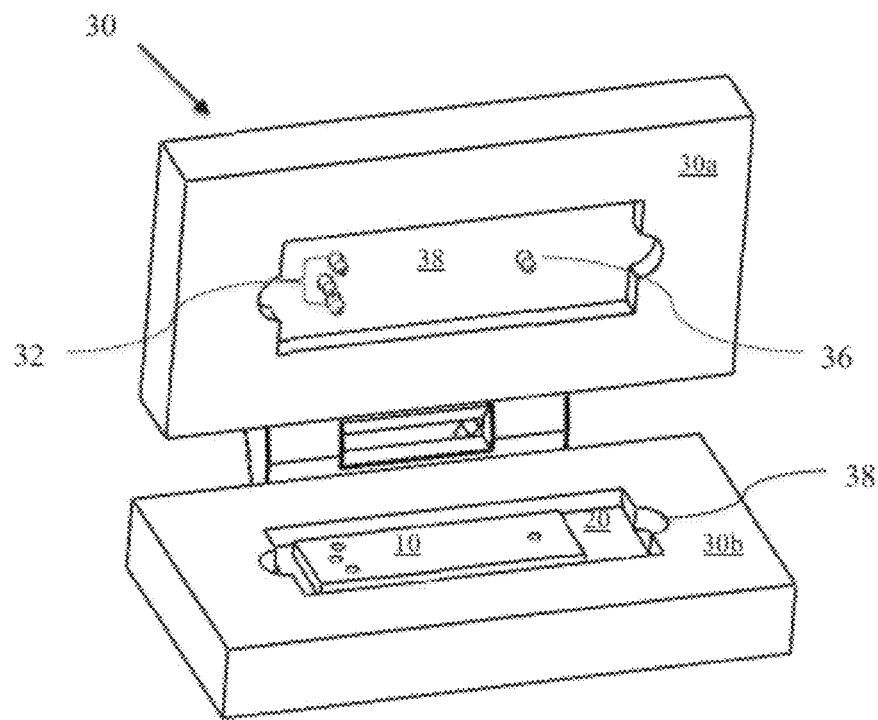
FIG. 13 is perspective view of a three-channel μCC overlay device, having three inlets and a single outlet, appended to a microscopic slide situated within the cavity, or chamber, of a μCC alignment fixture.
Figure 14:
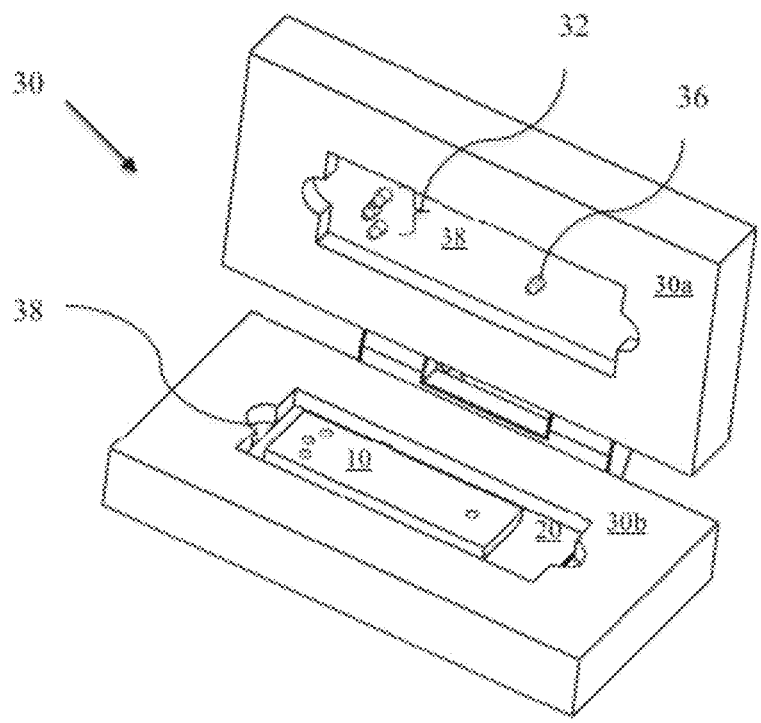
FIG. 14 is an alternative view of the device illustrated in FIG. 13.

FIG. 13 is an illustration of a μCC alignment fixture 30. The μCC alignment fixture 30 has opposing ends (30a and 30b) and a central cavity 38 that secures the μCC overlay device 10 and the microscopic slide 20, holding the device 10 and slide 20 securely against one-another as the opposing ends (30a and 30b) rotate closed. The μCC alignment fixture 30 also includes three inlet ports 32 and an outlet port 36 that are received by the respective inlets 12 and outlet 16 of the μCC overlay device 10, further securing the μCC overlay device 10 within the cavity 38 of the μCC alignment fixture 30. In addition to maintaining the proper relationship between the μCC overlay device 10 and the microscopic slide 20, the μCC alignment fixture 30 functions as a chamber that can be used to control temperature and humidity. FIG. 14 presents the μCC alignment fixture 30 illustrated in FIG. 13 from another angle.

Figure 15:
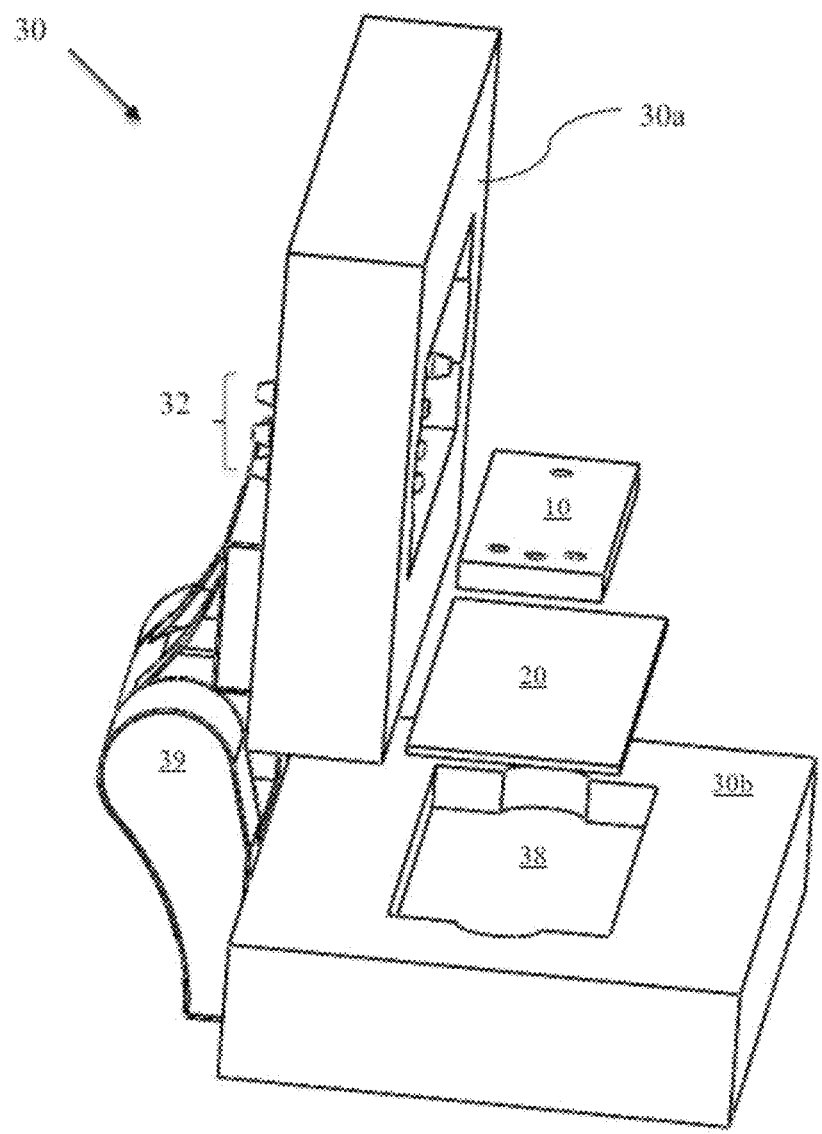
FIG. 15 is an alternative view of the device illustrated in FIG. 13, wherein the microscopic slide and the μCC overlay device are shown in proximity to an empty cavity.

FIG. 15 provides a further illustration of a μCC alignment fixture 30, with a μCC overlay device 10 and the microscopic slide 20, shown in proximity to, but not within, the cavity 38 of the μCC alignment fixture 30, as well as in proximity to one-another. Opposing ends (30a and 30b) are presented as rotated away from one-another along the axis provided by the hinge 39 of the μCC alignment fixture 30. The external ends of the three inlet ports 32 are also visible in FIG. 9.

Figure 16:
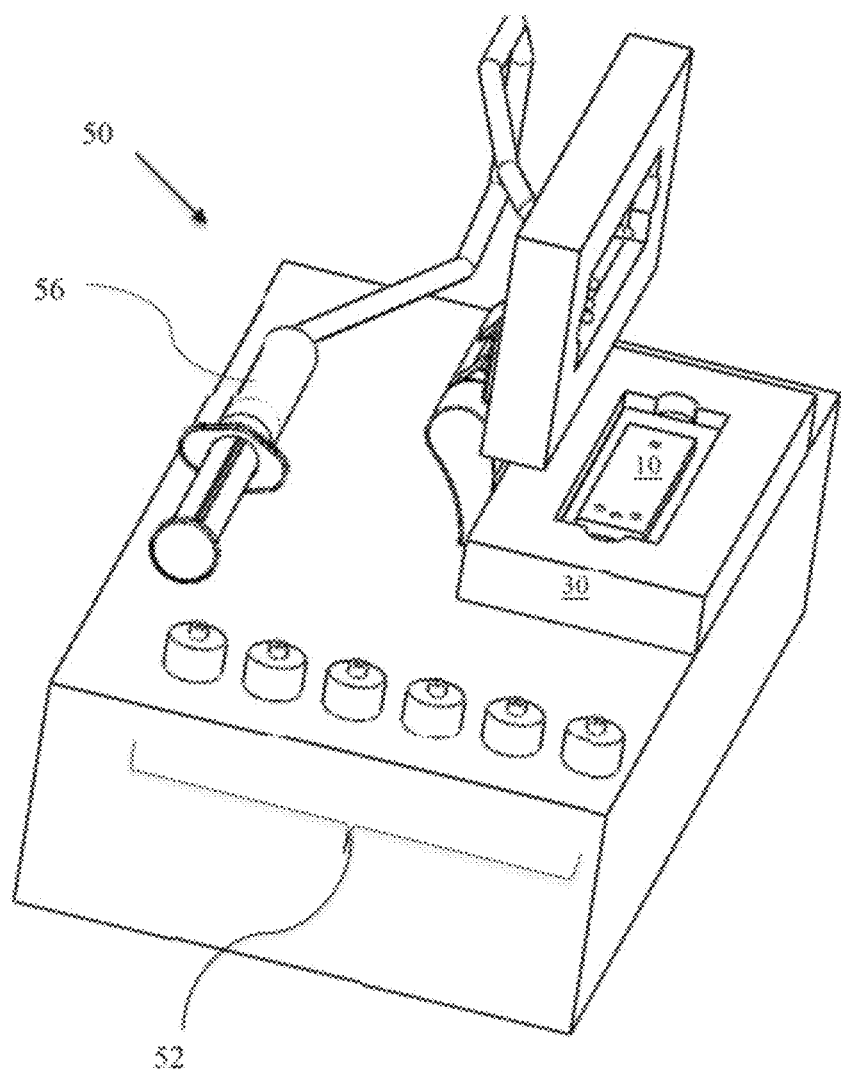
FIG. 16 is perspective view of a μCC staining device, having a μCC alignment fixture, with a μCC overlay device appended to a microscopic slide situated within the cavity of a μCC alignment fixture. The μCC staining device also has a plurality of reagent reservoirs and a pump.

FIG. 16 is an illustration of a μCC staining device 50. The μCC staining device 50 includes a plurality of reagent reservoirs 52 to store dyes, antibody and the like for staining the slide. A conduit (not shown), or tubing, would link the to an inlet port of the μCC alignment fixture 30, thereby delivering reagents to an inlet of the μCC overlay device 10. The pump 56 would supply the force to pull the reagent from the reagent reservoirs 52 through the staining device 50.

Figure 17:
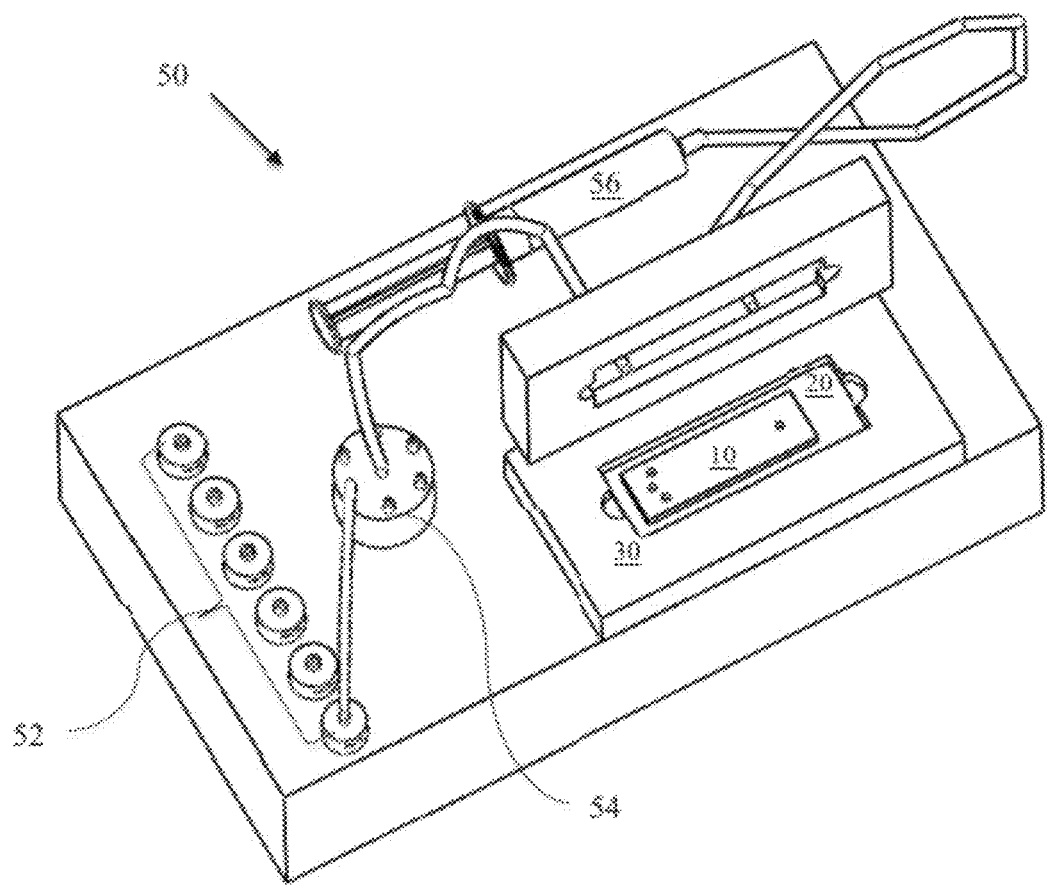
FIG. 17 is perspective view of a μCC staining device, having a μCC alignment fixture, with a μCC overlay device appended to a microscopic slide situated within the cavity of a μCC alignment fixture, a plurality of reagent reservoirs connected to a switching valve, the switching valve connected to the μCC alignment fixture and a pump, also connected to the μCC alignment fixture.
Figure 18:
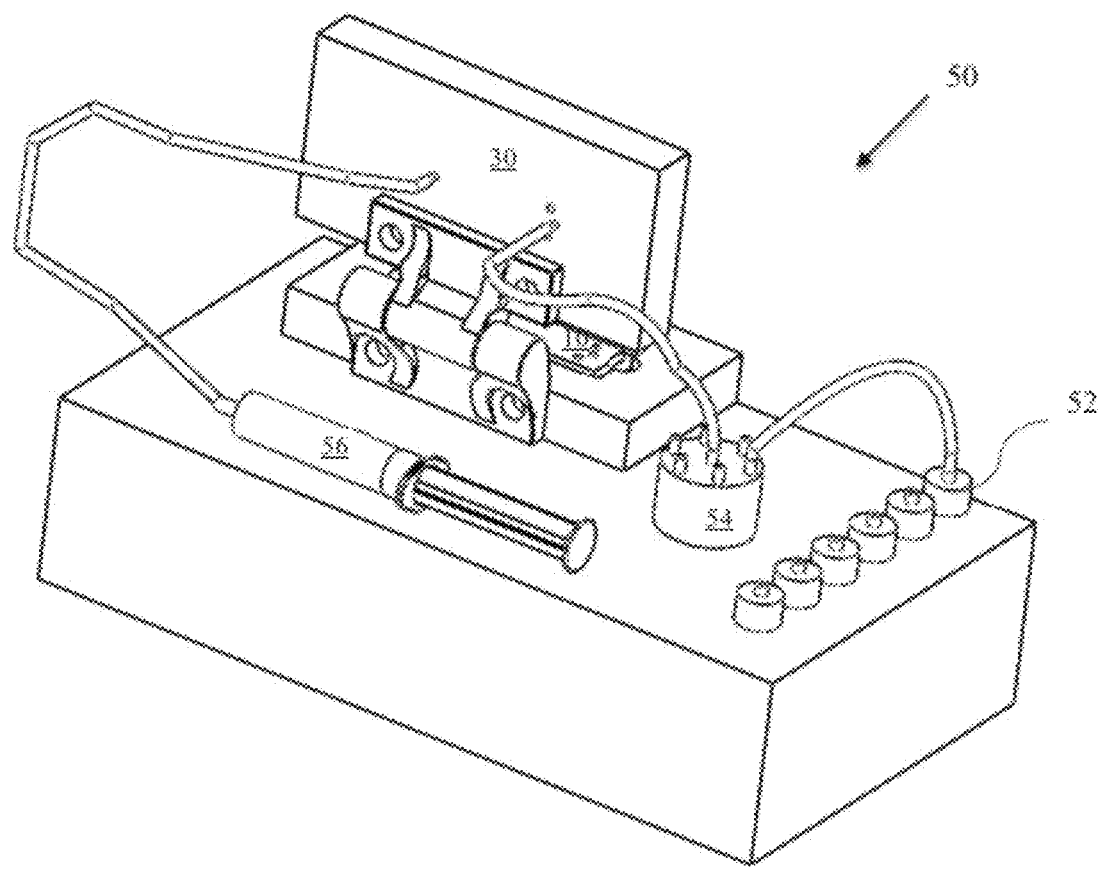
FIG. 18 is an alternative view of the device illustrated in FIG. 17.

FIG. 17 is an illustration of an alternative embodiment of a μCC staining device 50. The μCC staining device 50. In FIG. 17 adds a selector 54 to control delivery paths of the reagent from the reagent reservoirs 52 through the μCC alignment fixture 30 to the μCC overlay device 10. As illustrated in the schematics of FIGS. 23-26, a plurality of selectors can be employer. The use of selectors enables different reagents to be drawn into different channels at different times. This capacity allows different assays to be run on different parts of the μCC and to give multiple test results to the scientist or clinician. In effect, this allows each channel to function as a separate sample or instrument. Each assay will generally have different reagents and incubation times. This configuration enables a user to "multi-thread" the activities on different parts of the μCC overlay device. FIG. 18 is an additional illustration of the μCC staining device 50 illustrated in FIG. 17.

Figure 19:
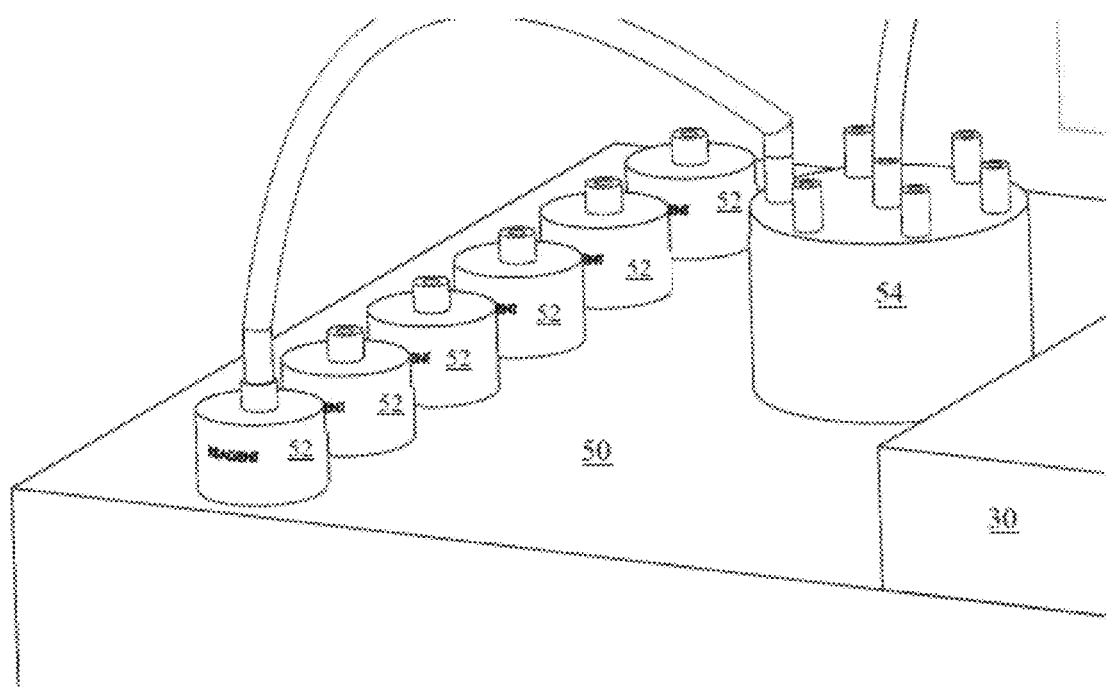
FIG. 19 is perspective view of a section of a μCC staining device, where one of the plurality of reagent reservoirs is connected to a switching valve.

FIG. 19 shows a portion of the μCC staining device 50 including the reagent reservoirs 52 through and the selector 54.

Figure 23:
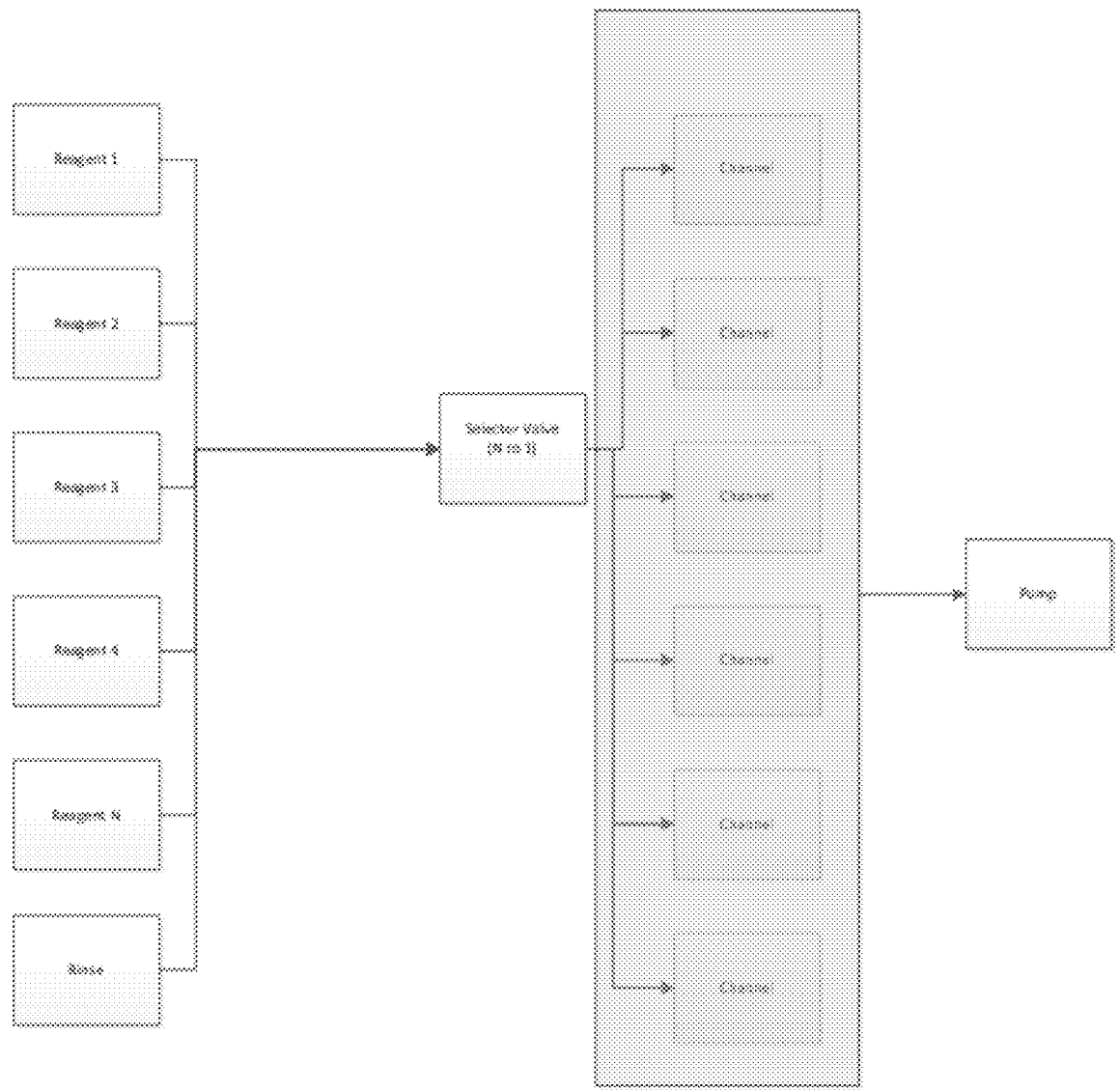
FIG. 23 is a flowchart illustrating potential fluidic schematics of a μCC staining device employing a μCC overlay device having five channels and a single outlet.
Figure 24:
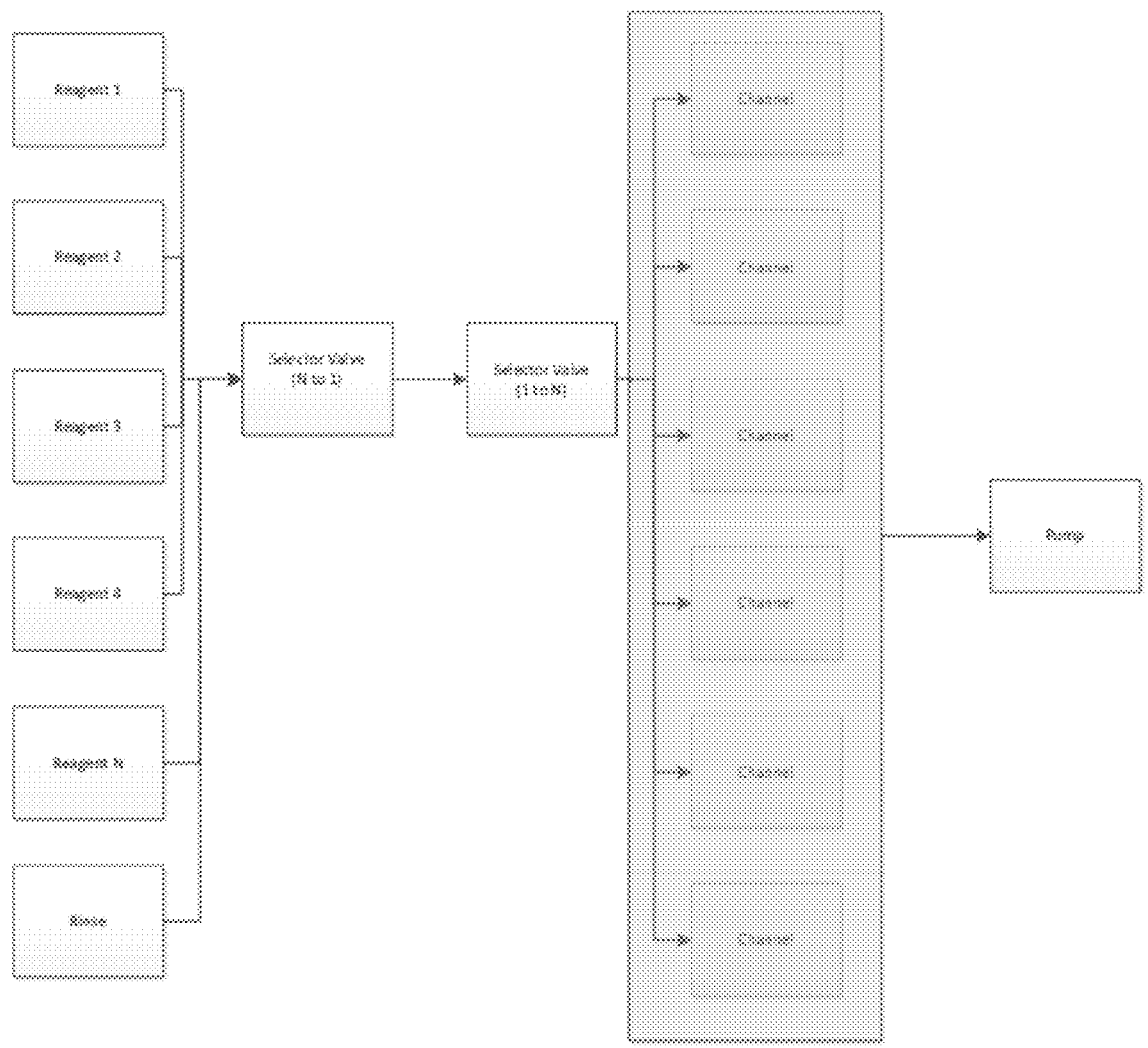
FIG. 24 is a flowchart illustrating potential fluidic schematics of a μCC staining device employing a μCC overlay device having five channels and a single outlet. The device illustrated in FIG. 24 utilizes an additional selector valve as compared to that illustrated in FIG. 23.
Figure 25:
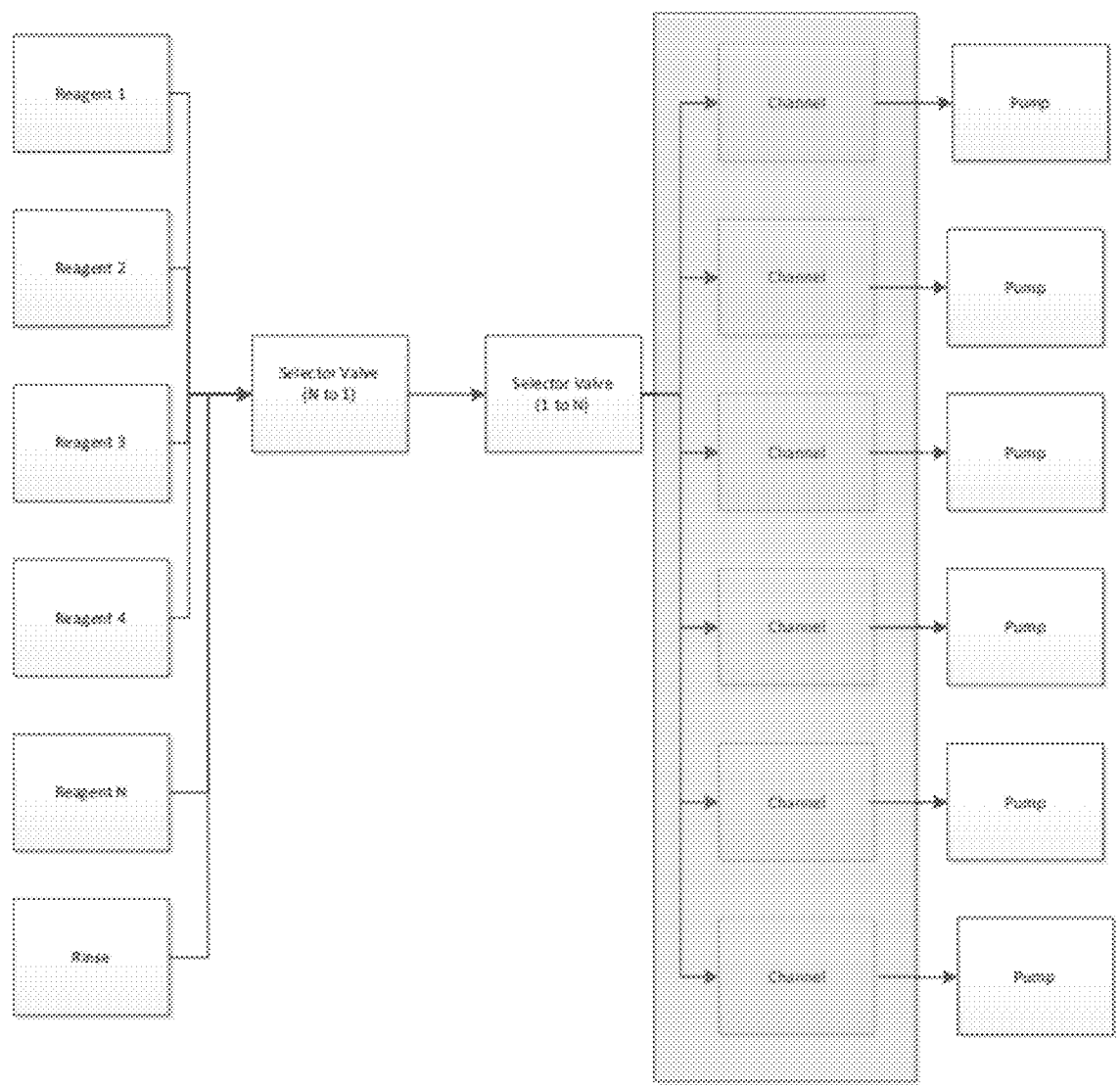
FIG. 25 is a flowchart illustrating potential fluidic schematics of a μCC staining device employing a μCC overlay device having five channels and a single outlet. The device illustrated in FIG. 25 utilizes a single pump for each of the five channels, as opposed to a single pump for all five channels as illustrated in FIG. 24.
Figure 26:
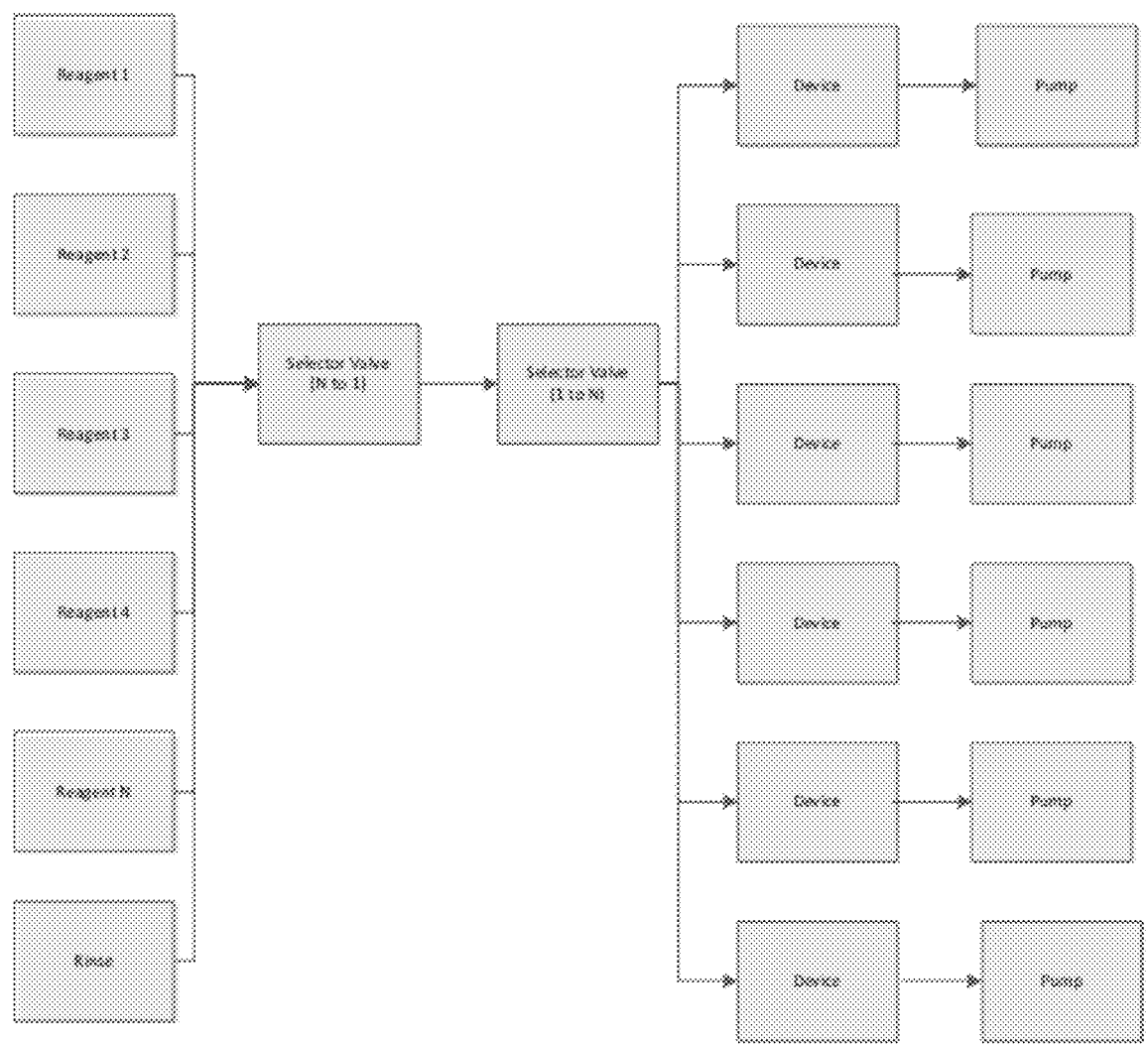
FIG. 26 is a flowchart illustrating potential fluidic schematics of a μCC staining device employing a μCC overlay device having five channels and a single outlet. The device illustrated in FIG. 26 has a single pump for each of the five channels, as opposed to a single pump for all five channels as illustrated in FIG. 24.

FIGS. 23-26 present a set of flowcharts illustrating potential fluidic schematics of increasing complexity. Capillary action can result in the mingling of reagent from one channel to another channel, which potentially clouds the results. The shaded box in FIGS. 23-25 represents the μCC overlay device and the schematic is illustrating that a user can choose to manifold (connect) fluidics in the μCC device or off of the device. Thus, it illustrates an additional embodiment to that of the prior figures.

DEFINITIONS

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

Kits for practicing the methods of the invention are further provided. By "kit" is intended any manufacture (e.g., a package or a container) comprising at least one reagent, e.g., a pH buffer of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The following examples are provided for the purpose of illustration and are not intended to limit the scope of the present invention.

Example 1

Materials and Methods

The following chemicals, biologicals, and supplies were used in the manufacturing and testing of this device: SU-8 3025 photoresist (Micro-Chem. Corp., Newton, Mass.), PDMS (Dow Corning, San Diego, Calif.), Sygard 184 elastomer curing agent (Dow Corning), methanol (Fisher, Pittsburgh, Pa.), triton X-100 (Fisher), acetone (Mallinckrodt Chemicals, Phillipsburg, N.J.), isopropyl alcohol (Mallinckrodt), hydrogen peroxide (Mallinckrodt), SuperBlock T20 (PBS) Blocking Buffer (Thermo Scientific, Rockford, Ill.), propylene glycol monomethyl ether acetate (Sigma-Aldrich, St. Louis, Mo.), 4-in. silicon wafers (Silicon Inc., Boise, Id.), IMEB Diff Stain Kit (San Marcos, Calif.), Histochemical Reaction Set—Ferric Iron (EMD Chemicals, Inc., Gibbstown, N.J.), 1×3 inch pre-cleaned glass micro slides (Corning Inc., Corning, N.Y.), 1×3 inch pre-cleaned glass microscope slides (Fisher), 10 mL syringes (Beckton Dickinson, Franklin Lakes, N.J.), 21 ga. 1 inch needles (Beckton Dickinson), Seamless Disposable Biopsy Punches (Robbins Instruments Inc., Chatham, N.J.), Polyclonal rabbit anti-human CD3 (Dako Denmark A/S, Glostrup, Denmark), Polyclonal rabbit anti-human FOXP1 (Abcam Inc., Cambridge, Mass.), Goat F(ab')2 polyclonal secondary antibody to rabbit IgG-Fc (HRP) (Abcam Inc.), Goat F(ab')2 polyclonal secondary antibody to mouse IgG-Fc (HRP) (Abcam Inc.), DAB Substrate Kit (Vector Laboratories, Inc., Burlingame, Calif.), Hematoxylin QS (Vector Laboratories, Inc.), ImmEdge Pen (Vector Laboratories, Inc.), VWR micro cover glass (VWR International, Radnor, Pa.), Lerner Aqua Mount (Thermo Scientific, Kalamazoo, Mich.), PHD 4400 Hpsi Programmable Syringe Pump (Harvard Apparatus, Holliston, Mass.).

Three easily obtainable tissue types were chosen for the initial testing on-chip. Canine blood films were prepared from excess blood available from samples submitted to the clinical pathology lab, College of Veterinary Medicine and Biomedical Sciences, Colorado State University, Fort Collins, Colo. In the same manner, extra pre-made canine bone marrow aspiration slides and lymph node imprints were also procured for use in this study. Samples were collected and prepared according to previously established procedures. [R. L. Cowell, *Diagnostic cytology and hematology of the dog and cat*, Mosby, St. Louis, Mo.; London, 2008] Before staining, prepared slides were air dried for at least one hour and subsequently fixed in absolute methanol or acetone for 10 minutes.

Example 2

μCC Device Fabrication

Polydimethylsiloxane (PDMS) μCC overlays were fabricated using SU-8 soft lithography methods published previously. [McDonald, J. C., et al., *Electrophoresis*, 2000, 21, 27-40; J. C. McDonald and G. M. Whitesides, *Acc Chem Res*, 2002, 35, 491-499; S. K. Sia and G. M. Whitesides, *Electrophoresis*, 2003, 24, 3563-3576; Liu, Y., et al., *Anal Chem*, 2000, 72, 5939-5944; Liu, Y., et al., *Anal Chem,* 2004, 76, 1513-1517; Liu, Y., et al., *Analyst,* 2001, 126, 1248-1251]

Briefly, PDMS molds were prepared on silicon wafers (Silicon Inc.) that were spin coated with SU-8 3025 photoresist (Microchem). The coated silicon wafer was covered with a photomask and exposed to UV light. The silicon wafer was then developed in propylene glycol monomethyl ether acetate (Sigma-Aldrich) leaving behind only [Banham, A. H., et al., *Clin Cancer Res,* 2005, 11, 1065-1072; Hoeller, S., et al., *Histopathology,* 2010, 57, 73-80] the desired features on the silicon wafer. Molds were prepared with three to five 50-120 μm high, 30.0-35.0 mm long channels that were separated by a distance of 1.0 mm (FIGS. 4 and 14-16). Molds with channel widths of 0.5 mm, 1.0 mm, 1.5 mm, 2.0 mm were created. For extraction, the polydimethylsiloxane (PDMS) microfluidic devices fabricated by the above procedure were placed in a triethylamine bath for two hours with constant stirring. The triethylamine was replaced with fresh solution after one hour. The PDMS microfluidic structures were then moved to an ethyl acetate bath for two hours with constant stirring and the ethyl acetate solution being replaced with fresh solution after one hour. The PDMS microfluidic structures were then moved to an acetone bath for two hours with constant stirring. After removal from the acetone bath the chips were placed in a 65° C. oven for a minimum of two hours.

In addition to fabricating the device from PDMS, it is envisioned that the device could be fabricated from extracted PDMS (see Example 5, below), PDMS+adhesive, and injection molded materials including rigid thermoplastic, rigid thermoplastic+elastomer, thermoplastic elastomer, thermoplastic+adhesive. It is further envisioned that force can be used to compress the μCC device to create a seal (see Example 5, below). The force can be supplied by a clip or other clamping device of the like. Another potential fabrication technique would be to mold a plastic chip and affix a laser cut adhesive onto its surface to form the channels. This creates sealing and a fluidics path at the same time.

Example 3

Immunocytochemistry Techniques Using the μCC Device

Immunocytochemistry (ICC) was carried out on slides based on techniques drawn from previously published methods. [Polak, J. M., and S. Van Noorden, *Introduction to immunocytochemistry,* BIOS Scientific Publishers, Oxford, 2003; Valli, V., et al., *Vet Clin Pathol,* 2009, 38, 261-269; Pettigrew, N. M., *Arch Pathol Lab Med,* 1989, 113, 641-644; Ponce, F., et al., *J Vet Diagn Invest,* 2003, 15, 330-337] All procedures detailed below were carried out at room temperature.

In brief, after fixation slides were air dried for at least one hour. After drying, slides were then treated with 0.1% Triton X100 (PBS) (Fisher) for 10 minutes. Slides were rinsed with PBS, then blocked (SuperBlock T20, Thermo Scientific) for 30 minutes. After blotting off of the blocking medium, slides were air dried for 30 minutes before mounting the respective μCC. Once mounted, fluid flow was established by injecting 10 μL PBS into each channel and subsequently applying suction at a rate of 10 μL/min/channel for 10 minutes (injecting additional PBS as needed). Flow was then stopped, and primary antibodies were loaded into their channels via 10 μL injection. Incubation was then carried out for 60 minutes at a rate of 0.3 μL/min/channel. Every 15 minutes channel wells were visually inspected and additional antibody added as needed. Channels were then rinsed for 5 minutes by applying a large bubble of PBS over the inlet wells and applying suction at a rate of 30 μL/min/channel. Endogenous peroxidase activity was then subsequently blocked by incubating with 3% $H_2O_2$ for 15 minutes at 30 μL/min/channel. Another 5-minute PBS rinse was carried out, and flow was then stopped to add appropriate secondary antibody. As with primary antibody, 10 μL secondary was added and run for 30 minutes at 0.3 μL/min/channel. After 5 minutes of PBS rinsing at a rate of 30 μL/min/channel, DAB substrate (Vector Laboratories, Inc.) was added for 2 minutes at 30 μL/min/channel. Channels were then flushed with dH20 for 5 minutes at 30 μL/min/channel. Hematoxylin counter stain (Vector Laboratories, Inc.) was then run for 2 minutes at 30 μL/min/channel, followed by another 5 minute dH20 rinse. The μCC was then removed and the slides allowed to dry. After drying, slides were cover slipped (VWR International) using an aqueous mounting medium (Thermo Scientific), allowed to set, and then examined using brightfield microscopy.

Example 4

μCC Device to Stain Fixed Tissue Samples

Figure 28A:
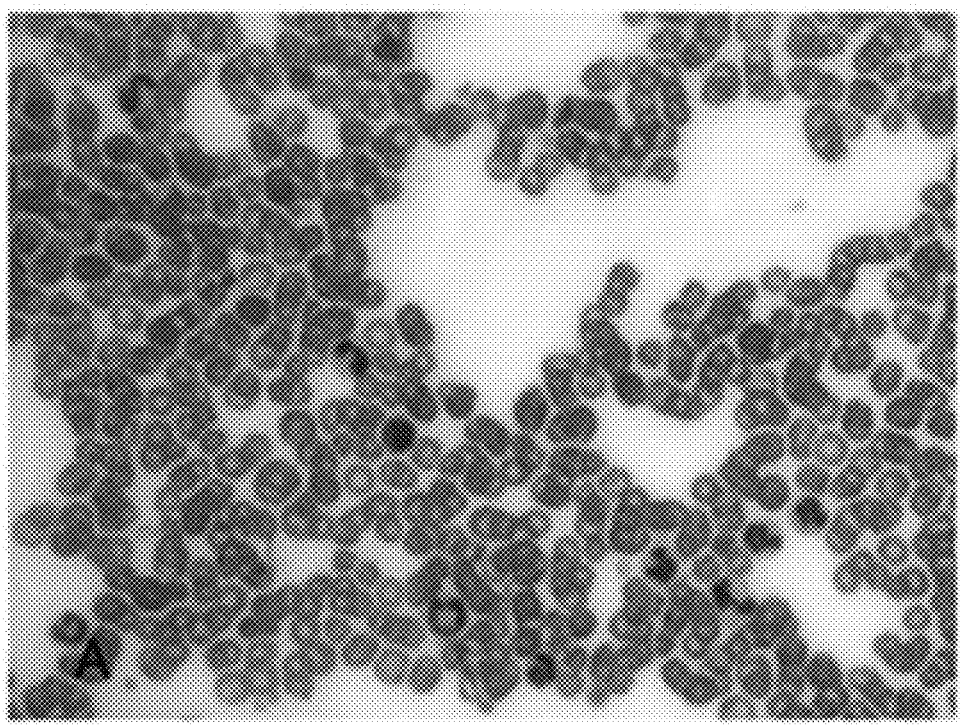
FIG. 28 is a pair of images illustrating a comparison of staining using a μCC overlay device vs. existing methods. (A) Blood film stained with Diff Stain Kit, IMEB, San Marcos, Calif. (40× Objective). (B) Blood film stained with automated stainer, Wright-Giemsa stain (40× Objective). While variations of Romanowsky stains were used in these two images, they illustrate the staining quality that can be achieved in a μCC format involving smaller reagent volumes (μL vs. mL) and reaction times (2-3 min. per slide vs. 6 min. per slide).
Figure 28B:
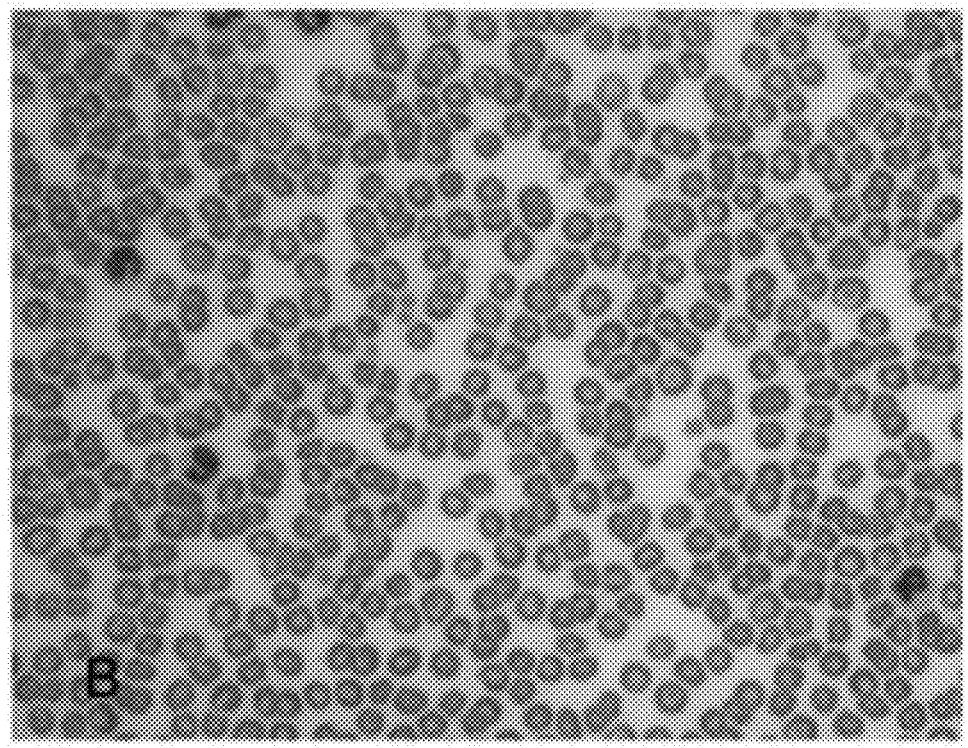

For the initial trials a chip with channel widths of 1 mm was used, the channel design of which is identical to that illustrated in FIGS. 20 and 22. Using 1 mm wide channels provides roughly a 60 $mm^2$ staining area per channel. Morphological staining was carried out using a modified procedure via an IMEB Diff Stain Kit based on previously described procedures. [Potvin, C. A., *Laboratory Medicine,* 1994, 25, 389-391] Iron staining was also carried out in an adjacent channel according to previously reported procedures. [Gomori, G., *Am J Pathol,* 1936, 12, 655-664 651; H. Bunting, *Stain Technol,* 1949, 24, 109-115] Staining results comparing currently used staining procedures and the procedures described here are shown in FIGS. 28B and 28A, respectively. The results from these studies clearly show the ability of the μCC to perform staining of the tissue samples fixed on a single slide. Furthermore, each channel consumed approximately 10 μL of stain, while commonly used automated stainers and protocols rely on milliliters to liters of stain. Finally, the total staining time for the microfluidic device was approximately 5 minutes, which is significantly shorter than the 12-25 min typically required.

Example 5

Producing Hydrophilic PDMS μCC Devices

Figure 27:
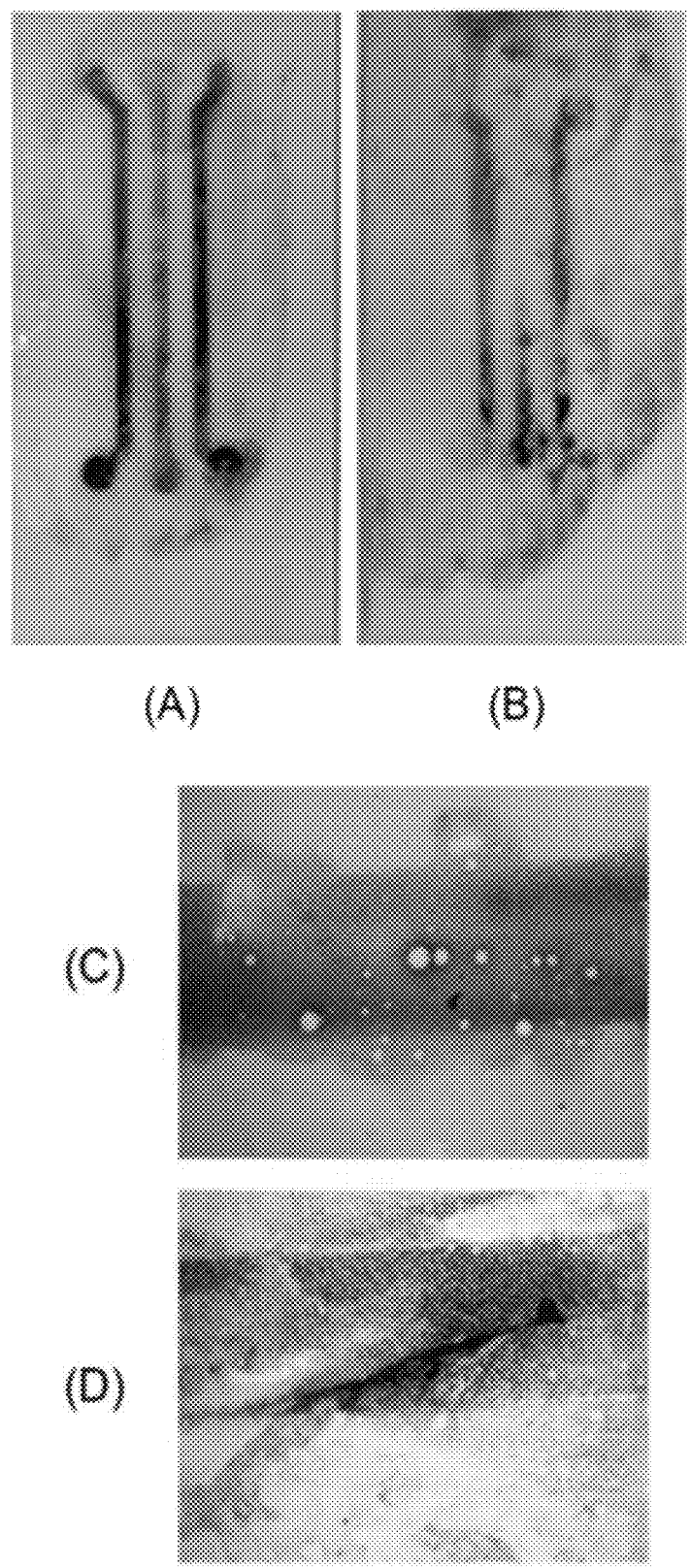
FIG. 27 is a set of images illustrating the differences between extracted and non-extracted PDMS μCC overlay devices. (A) Bone marrow FNA—10:1 Non-extracted PDMS chip, 1000 nM channel width; (B) Bone marrow FNA—10:1 Extracted PDMS chip, 1000 nM channel width; (C) Bone marrow FNA (40× objective)—10:1 Non-extracted PDMS chip, 1000 nM channel width; (D) Bone marrow FNA (40× objective)—10:1 Extracted PDMS chip, 1000 nM channel width. All slides stained with Diff Stain Kit, IMEB San Marcos, Calif.

While the preliminary staining results were very encouraging, significant leakage of the stain from the channels to surrounding tissue occurred, evidence of which is illustrated in FIGS. 27A-D (especially in the higher magnified image of FIG. 27C). While not a major concern with the current channel separation of 1 mm, leakage could become problematic when higher density channel networks are used, as mixing stains is detrimental to proper tissue examination. This leakage was attributed to poor adhesion between the PDMS overlay and the underlying tissue on the slide. As a material, PDMS is inherently hydrophobic and does not adhere well to wetted cytology slides. This hydrophobicity can be attributed to the migration of residual low molecular weight non-crosslinked oligomers within the bulk PDMS to the surface following curing. [Fritz, J. L. and M. J. Owen, *The Journal of Adhesion,* 2012, 54, 33-45; Kim, J., et al., *Journal of Colloid and Interface Science,* 2000, 226, 231-236; Kim, J., et al., *Journal of Colloid and Interface Science,* 2001, 244, 200-207] To address these issues a method for the removal of these oligomers through extraction was utilized. [Vickers, J. A., et al., *Anal Chem,* 2006, 78, 7446-7452] After plasma treating the extracted PDMS, the material becomes hydrophilic and stays this way for weeks without retreatment. To determine if PDMS hydrophobicity was a limiting factor in the ability to contain stains to the microfluidic channels extracted PDMS chips was compared to "normal" non-extracted chips. FIG. 27C (non-extracted) shows a tissue slide stained with the same morphological stain shown in FIG. 27D (extracted). It can be clearly seen that leakage is markedly reduced by making the PDMS hydrophilic. This finding is important because it will allows the development of higher density channel networks in the future, increasing the staining density and/or the number of stains used on a single slide.

Example 6

Immunostaining with μCC Devices

Figure 29:
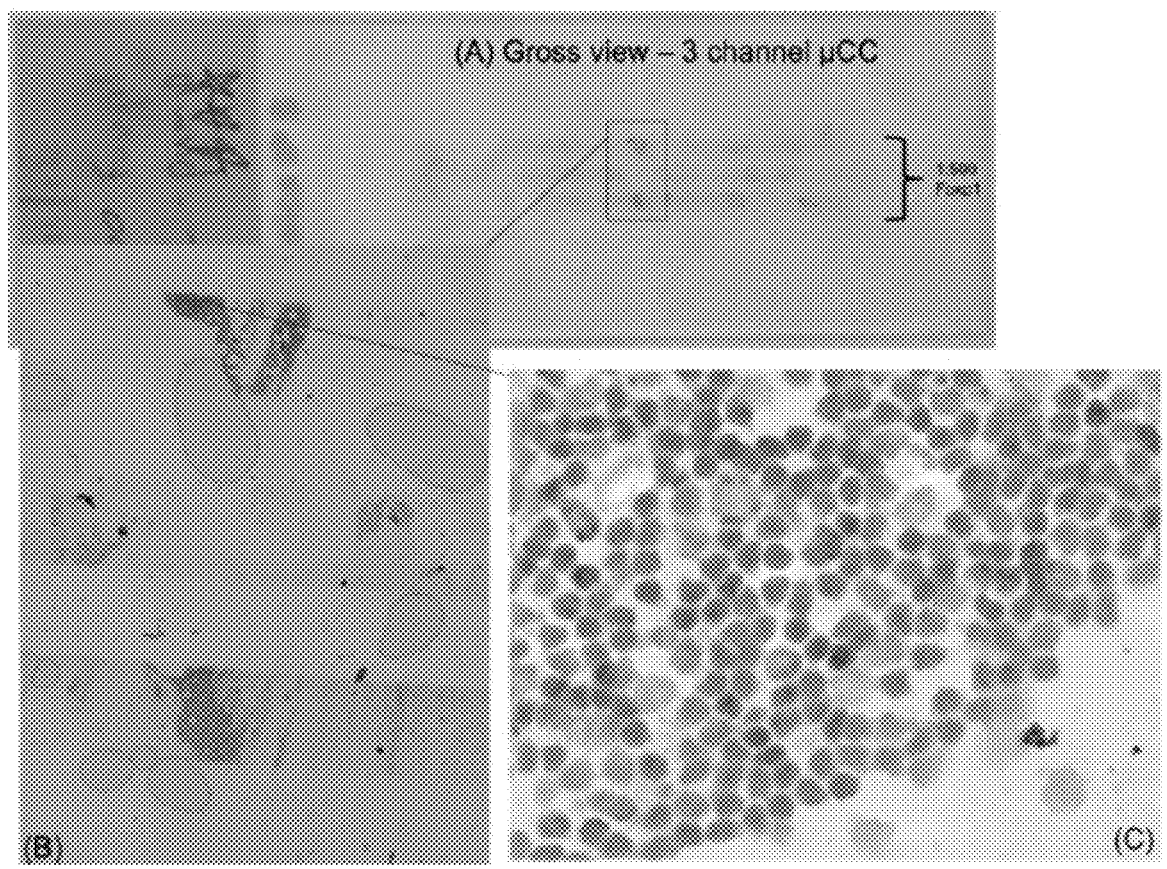
FIG. 29 is a set of images illustrating immunostaining with a μCC overlay device. The figure illustrates anti-Foxp1 staining of acetone fixed lymph node imprints using a parallel, 3 channel, 1 mm width, single outlet chip. Fluid movement is enabled via the use of a syringe pump. (A) Gross view of the resulting μCC-stained slide. (B) 20× original magnification view of channel fidelity. Note the lack of leakage beyond channel borders. (C) Positive Foxp1 immunostaining (1,000× original magnification).
Figure 30:
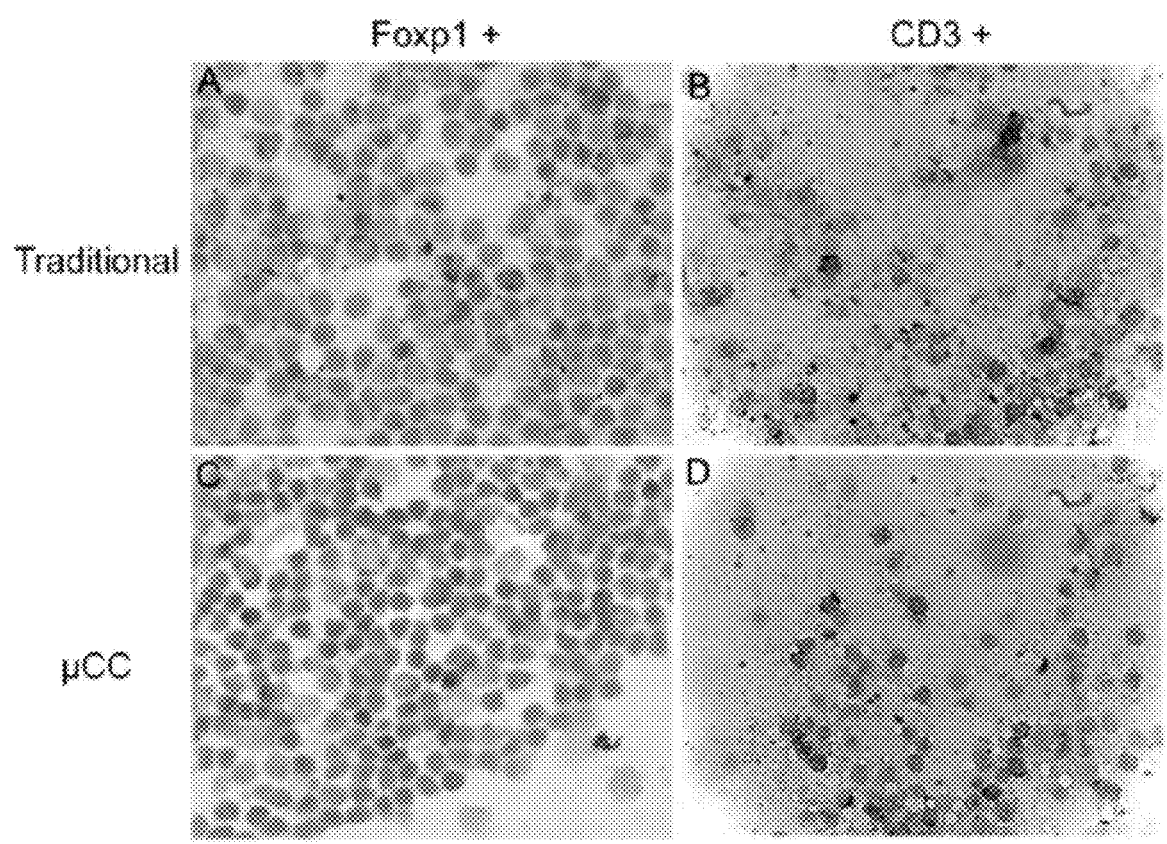
FIG. 30 is a set of images illustrating a comparison of immunostaining using the μCC chip relative to existing methods. Positively stained cells appear dark grey to black in the grey-scale images. (A) Lymph node stained with anti-Foxp1 antibody using traditional, whole slide methods (1,000×). (B) Lymph node stained with anti-CD3 antibody using traditional, whole slide methods (400×). (C) Lymph node stained with anti-Foxp1 antibody using a 1 mm wide, 3 parallel channel μCC (1,000×). (D) Lymph node stained with anti-CD3 antibody using a 1 mm wide, 3 parallel channel μCC (400×). All slides stained using a secondary antibody-HRP DAB system with hematoxylin counterstaining.

To evaluate the ability of the μCC device to perform immunostaining, immunocytochemistry (ICC) was conducted on unstained canine lymph node imprints. For the first test CD3 was chosen, a protein that associates with the T-cell receptor, and which is commonly used to identify healthy and cancerous T-cells in both humans and companion animals. [R. A. Goldsby, *Immunology,* W.H. Freeman, New York, 2003] Using a 1 cc syringe to provide gentle suction and fluid exchange, ICC was performed using the 3 parallel channel chip shown in FIGS. 20 and 22. As seen in FIGS. 30B and 30D, results using the μCC device are comparable to traditional, whole slide methods. We then tested another marker known as Foxp1, a transcription factor that is used to establish prognosis in cases of B-cell lymphoma. [Banham, A. H., et al., *Clin Cancer Res,* 2005, 11, 1065-1072; Hoeller, S., et al., *Histopathology,* 2010, 57, 73-80] For this test we modified our 3 parallel channel design (FIGS. 14 and 16) into 3 and 5 channel single outlet chips (FIGS. 4 and 15). This enabled us to use a syringe pump connected to the single outlet port of our chip to provide automated fluid flow instead of the more cumbersome manual method used previously. As seen in FIGS. 29, 30A, and 30C, we were also able to obtain comparable staining with traditional methods using this marker. Furthermore, this experiment demonstrated the ability of the μCC to couple with automated methods, an important consideration in the future development of this device. This also appears to be the first reported instance of Foxp1 staining in canine lymphoid tissue, which supports a role in using this device for future antibody screening of both novel tissue and antibody types.

This μCC design represents a fundamentally new approach to performing cytology staining and examination, and is a novel application of PDMS-based microfluidics. The method will allow conservation of sample, reagents, and allow for faster diagnosis, ultimately allowing for better patient outcomes. In addition, this work will open many new doors for analysis of similar types of samples for other disease states. It is envisioned that this platform will be applicable to many other types of clinical samples beyond blood, bone marrow, and lymphoid tissue; providing for faster, more efficient diagnosis and phenotyping of many disease types. Future applications of this multiplexing technology should greatly enrich the fields of biomarker discovery and antibody screening.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A microfluidic overlay device comprising:
   a first substantially planar and substantially rectangular surface comprising:
   a plurality of first ports adapted to receive a fluid, the ports spaced adjacent to one edge of the first surface; and
   a plurality of channels extending from the first ports, wherein the number of channels corresponds to the number of first ports; and
   a second surface opposite the first surface, the second surface comprising:
   a plurality of channels linearly extending in parallel across the second surface; and
   a plurality of second ports adapted to facilitate egress of the fluid, wherein the second ports are in fluid communication with the second surface channels; and
   conduits, wherein each conduit provides fluid communication between a single first surface channel and a single second surface channel and the number of conduits corresponds to the number of channels on the first surface.

2. The microfluidic overlay device according to claim 1 wherein the channels on the second surface are substantially straight.

3. The microfluidic overlay device according to claim 1 wherein the channels on the first surface are perpendicular to channels on the second surface.

4. The microfluidic overlay device according to claim 1 where the first ports are reservoirs sized to receive and store the fluid.

5. The microfluidic overlay device according to claim 1 wherein each of the plurality of second surface channels forms a sealed channel extending between a conduit and a second port of the microfluidic overlay device when the device is coupled to a solid surface.

6. The microfluidic overlay device according to claim 1 further comprising a coupling device to affix the microfluidic overlay device to a microscopic slide.

7. The microfluidic overlay device according to claim 6 wherein the coupling device is selected from the group consisting of a clip, a sleeve, and a chamber.

8. The microfluidic overlay device according to claim 1 wherein each of the plurality of channels is 50 to 120 μm high and 0.5 mm to 2.0 mm wide.

9. The microfluidic overlay device according to claim 1 wherein the first surface ports are equidistantly spaced from the one edge of the first surface.

10. A microfluidic overlay device comprising:
    a first substantially planar and substantially rectangular surface comprising:
    a plurality of first ports adapted to receive a fluid, the ports spaced adjacent to one edge of the first surface; and
    a plurality of channels extending from the first ports, wherein the number of channels corresponds to the number of first ports;

a second surface opposite the first surface, the second surface comprising:
: a plurality of channels extending across the second surface; and
: a second port adapted to facilitate egress of the fluid, wherein the second port is in fluid communication with the second surface channels; and conduits, wherein each conduit provides fluid communication between a single first surface channel and a single second surface channel and the number of conduits corresponds to the number of channels on the first surface.

11. The microfluidic overlay device according to claim 10 wherein the channels on the second surface are substantially straight.

12. The microfluidic overlay device according to claim 10 wherein the channels on the first surface are perpendicular to channels on the second surface.

13. The microfluidic overlay device according to claim 10 wherein the second port opens through the first surface of the overlay device, thereby allowing ingress and egress of the fluid through the first surface of the overlay device.

14. The microfluidic overlay device according to claim 10 wherein each of the plurality of channels is 50 to 120 μm high and 0.5 mm to 2.0 mm wide.

15. The microfluidic overlay device according to claim 10 wherein the first surface ports are equidistantly spaced from the one edge of the first surface.

16. A microfluidic overlay device comprising:
: a first substantially planar and substantially rectangular surface comprising:
:: a plurality of first ports adapted to receive a fluid, the ports spaced adjacent to one edge of the first surface; and
:: a plurality of channels extending from the first ports, wherein the number of channels corresponds to the number of first ports; and
: a second surface comprising:
:: a plurality of channels linearly extending in parallel across the surface of the second surface; and
:: a plurality of second ports adapted to facilitate egress of the fluid, wherein the second ports are in fluid communication with the second surface channels and the second ports open through the first surface of the overlay device, thereby allowing ingress and egress of the fluid through the first surface of the overlay device; and conduits, wherein each conduit provides fluid communication between a single first surface channel and a single second surface channel and the number of conduits corresponds to the number of channels on the first surface.

17. The microfluidic overlay device according to claim 16 wherein the channels on the second surface are substantially straight.

18. The microfluidic overlay device according to claim 16 wherein the channels on the first surface are perpendicular to channels on the second surface.

19. The microfluidic overlay device according to claim 16 wherein the first surface ports are equidistantly spaced from the one edge of the first surface.

\* \* \* \* \*